(12) United States Patent
Hwang et al.

(10) Patent No.: US 10,821,153 B2
(45) Date of Patent: Nov. 3, 2020

(54) COMPOSITION FOR IMPROVING MUSCULAR FUNCTION OR FOR ENHANCING EXERCISE PERFORMANCE COMPRISING VIGNA ANGULARIS VAR. ANGULARIS

(71) Applicant: NEWTREE CO., LTD., Jungwon-gu, Seongnam-si (KR)

(72) Inventors: Jae Kwan Hwang, Seoul (KR); Se In Lee, Seoul (KR); Mi Bo Kim, Seoul (KR); Chang Hee Kim, Seoul (KR); Doun Kim, Seongnam-si (KR); Heechul Chung, Seongnam-si (KR); Hyeongmin Kim, Seoul (KR)

(73) Assignee: NEWTREE CO., LTD., Seongnam-si, Gyeonggi-Do (KR)

( * ) Notice: Subject to any disclaimer, the term of this patent is extended or adjusted under 35 U.S.C. 154(b) by 131 days.

(21) Appl. No.: 16/098,416

(22) PCT Filed: May 2, 2017

(86) PCT No.: PCT/KR2017/004701
§ 371 (c)(1),
(2) Date: Nov. 1, 2018

(87) PCT Pub. No.: WO2017/192013
PCT Pub. Date: Nov. 9, 2017

(65) Prior Publication Data
US 2019/0142897 A1    May 16, 2019

(30) Foreign Application Priority Data

May 2, 2016 (KR) .......... 10-2016-0054290
May 2, 2017 (KR) .......... 10-2017-0056162

(51) Int. Cl.
*A61K 36/48* (2006.01)
*A61K 38/16* (2006.01)
(Continued)

(52) U.S. Cl.
CPC ............ *A61K 38/168* (2013.01); *A21D 2/362* (2013.01); *A23B 7/024* (2013.01); *A23G 3/44* (2013.01);
(Continued)

(58) Field of Classification Search
CPC ...................................................... A61K 36/48
See application file for complete search history.

(56) References Cited

U.S. PATENT DOCUMENTS

2002/0068124 A1    6/2002 Endo
2008/0096243 A1    4/2008 Cho et al.

FOREIGN PATENT DOCUMENTS

CN     104293869 A    1/2015
CN     104304711 A    1/2015
(Continued)

OTHER PUBLICATIONS

Google Patents English-language translation of Shiseido Co. Ltd., JP 2007-230965 A, 2007.*
(Continued)

*Primary Examiner* — Rosanne Kosson
(74) *Attorney, Agent, or Firm* — James S. Keddie; Bozicevic, Field & Francis LLP

(57) ABSTRACT

*Vigna angularis* var. *angularis* according to the present invention is capable of increasing muscle mass and enhancing muscular function or exercise performance through an effect of promoting mRNA or protein expression and the activity of a gene involved in muscle functions, muscle mass increase of differentiation of muscle cells; can prevent, treat or ameliorate a decline in exercise performance, a decline in
(Continued)

muscle function, muscle loss, etc. caused by various diseases; and may be effectively used for medicines or food products, etc., since it has no side effects in the body as natural substance.

8 Claims, 14 Drawing Sheets

Specification includes a Sequence Listing.

(51) Int. Cl.
| | |
|---|---|
| A23L 33/105 | (2016.01) |
| A23G 4/06 | (2006.01) |
| A21D 2/36 | (2006.01) |
| A23L 2/66 | (2006.01) |
| A23G 3/44 | (2006.01) |
| A23G 3/48 | (2006.01) |
| A23L 2/52 | (2006.01) |
| A61P 21/00 | (2006.01) |
| A23B 7/024 | (2006.01) |
| A23J 3/34 | (2006.01) |
| A61K 9/14 | (2006.01) |
| A61K 9/20 | (2006.01) |
| A61K 9/48 | (2006.01) |
| B01D 11/02 | (2006.01) |
| B01D 21/26 | (2006.01) |

(52) U.S. Cl.
CPC ............... *A23G 3/48* (2013.01); *A23G 4/068* (2013.01); *A23J 3/346* (2013.01); *A23L 2/52* (2013.01); *A23L 2/66* (2013.01); *A23L 33/105* (2016.08); *A61K 9/14* (2013.01); *A61K 9/2095* (2013.01); *A61K 9/4833* (2013.01); *A61K 36/48* (2013.01); *A61P 21/00* (2018.01); *B01D 11/0288* (2013.01); *B01D 21/262* (2013.01); *A23V 2002/00* (2013.01); *A61K 2236/00* (2013.01)

(56) References Cited

FOREIGN PATENT DOCUMENTS

| | | |
|---|---|---|
| CN | 105105249 A | 12/2015 |
| EP | 2322208 A2 | 5/2011 |
| JP | 61-093124 A | 5/1986 |
| JP | 2007230965 A | 9/2007 |
| JP | 2014091686 A | 5/2014 |
| KR | 20020044535 A | 6/2002 |
| KR | 1020020044535 | 1/2007 |
| KR | 20070117151 A | 12/2007 |
| KR | 20170002846 A | 1/2017 |

OTHER PUBLICATIONS

Bibliographic information for Shiseido Co. Ltd., JP 2007-230965 A, 2007.*

Kim, et al., "Inhibitory Effect of Red Bean Extract on TNF-α-induced Muscle Atrophy in Skeletal Muscle Cells", Journal of the Korean Society of Food Science and Nutrition, abstract No. P09-385, Oct. 2016, pp. 491-492.

Wati et al., "Trypsin Inhibitor from 3 Legume Seeds: Fractionation and Proteolytic Inhibition Study", Journal of Food Science, 2010, 75(3): C223-C228.

* cited by examiner red bean peptide (µg/mL)

50   100

MyoD

Myogenin

β-Actin

SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide Atrogin_F

<400> SEQUENCE: 1
gtccagagag tcggcaagtc                                                       20

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide Atrogin_R

<400> SEQUENCE: 2
gtcggtgatc gtgagacctt                                                       20

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide MuRF_F

<400> SEQUENCE: 3
tctactcggc cacaggcgct                                                       20

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide MuRF_R

<400> SEQUENCE: 4
cttgacagct cccgccgcaa                                                       20

<210> SEQ ID NO 5
<211> LENGTH: 22
<212> TYPE: DNA
<213> ORGANISM: Artificial Sequence
<220> FEATURE:
<223> OTHER INFORMATION: synthetic oligonucleotide Actin_F

<400> SEQUENCE: 5
ctgtgtggat tggtggctct at                                                    22

<210> SEQ ID NO 6
<211> LENGTH: 23
<212> TYPE: DNA
<213> ORGANISM: Artificial Sequence
<220> FEATURE:
<223> OTHER INFORMATION: synthetic oligonucleotide Actin_R

<400> SEQUENCE: 6
gtgtaaaacg cagctcagta aca                                                   23

<210> SEQ ID NO 7
<211> LENGTH: 20
<212> TYPE: DNA
<213> ORGANISM: Artificial Sequence

```
<220> FEATURE:
<223> OTHER INFORMATION: synthetic oligonucleotide MyoD_F

<400> SEQUENCE: 7
ggatggtgcc cctgggtcct                                              20

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide MyoD_R

<400> SEQUENCE: 8
tggccttcgc tgtgagtcgc                                              20

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide Myogenin_F

<400> SEQUENCE: 9
tgggctgcca caagccagac                                              20

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide Myogenin_R

<400> SEQUENCE: 10
cagcccagcc actggcatca                                              20

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide PGC_F

<400> SEQUENCE: 11
atgtgtcgcc ttcttgctct                                              20

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide PGC_R

<400> SEQUENCE: 12
atctactgcc tggggacctt                                              20

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide ERR_F

<400> SEQUENCE: 13
aaggggatgg agaccacagt                                              20
```

```
<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide ERR_R

<400> SEQUENCE: 14
tgaggtggga gctgataggg                                              20

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide NRF_F

<400> SEQUENCE: 15
tggacccaag cattacggac                                              20

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide NRF_R

<400> SEQUENCE: 16
ggtcatttca ccgccctgta                                              20

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide Tfam_F

<400> SEQUENCE: 17
gcttccagga ggctaaggat                                              20

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide Tfam_R

<400> SEQUENCE: 18
cccaatccca atgacaactc                                              20
```

COMPOSITION FOR IMPROVING MUSCULAR FUNCTION OR FOR ENHANCING EXERCISE PERFORMANCE COMPRISING VIGNA ANGULARIS VAR. ANGULARIS

CROSS-REFERENCE TO RELATED APPLICATIONS

This application is a § 371 national phase of International Application No. PCT/KR2017/004701, filed on May 2, 2017, which claims the benefit of Korean Patent Application Nos. 10-2016-0054290 filed May 2, 2016, and 10-2017-0056162, filed May 2, 2017, which applications are incorporated by reference herein.

TECHNICAL FIELD

The present invention relates to a composition for improving muscular function or for enhancing exercise performance comprising red bean extract, red bean-derived protein and red bean-derived peptide as an active ingredient, respectively.

BACKGROUND OF THE INVENTION

Muscle atrophy, which is caused by a gradual decrease in muscle mass, refers to muscle weakness and degeneration (Cell, 119(7): 907-910, 2004). Muscle atrophy is caused by inactivity, oxidative stress, chronic inflammation and so on, and weakens muscle function and exercise performance (Clinical Nutrition, 26(5): 524-534, 2007).

In this regard, the most important factor for determining muscle function is muscle mass, which is maintained by the balance of muscle protein synthesis and protein degradation. Muscle atrophy occurs when protein degradation exceeds protein synthesis (The International Journal of Biochemistry and Cell Biology, 37(10): 1985-1996, 2005).

Muscle size is controlled by the intracellular signaling pathways that lead to anabolism or catabolism in the muscles. When signaling reactions for the synthesis of muscle proteins exceed those for the degradation of muscle proteins, muscle protein synthesis is increased, resulting in increased muscle size (hypertrophy) or increased number of muscle fiber (hyperplasia) as the muscle protein increases (The Korea Journal of Sports Science, 20(3): 1551-1561, 2011).

Hypertrophy-inducing factors trigger protein synthesis by phosphorylating downstream proteins from the stimulation of phosphatidylinositol-3 kinase (PI3K)/Akt pathway in myocytes. Of these, the activity of mammalian target of rapamycin (mTOR) by PI3K/Akt signaling is recognized as a major growth signaling mechanism that integrates various intracellular growth signals. Activation of mTOR may contribute to increase in muscle mass by inducing muscle protein synthesis through activating two downstream targets, i.e, 4E-binding protein (4EBP1) and phosphorylated 70-kDa ribosomal S6 kinase (p70S6K) (The Korea Journal of Sports Science, 20(3): 1551-1561, 2011; The International Journal of Biochemistry and Cell Biology, 43(9): 1267-1276, 2011).

Conversely, when forhead box (FoxO), a transcription factor, migrates from the cytoplasm to the nucleus in a cell, it increases the expression of E3 ubiquitin ligase factors atrogin-1 and MuRF-1, which are involved in protein degradation (Disease Models & Mechanisms, 6: 25-39, 2013). When their expression level, increase protein degradation in the muscle is promoted and muscle mass is reduced. Thus, activation of mTOR, inhibition of atrogin-1 and MuRF-1 expression increase muscle mass by increasing the amount of muscle protein.

In addition, muscle cell differentiation and muscle formation can be controlled by a variety of muscle regulatory factors. Among them, MyoD promotes the process during which myoblasts become myotubes through the induction of myogenin expression. The muscle fiber formed through this process forms bundles and finally forms muscles (Cellular and Molecular Life Sciences, 70: 4117-4130, 2013).

One of the representative pulse crops, red bean (*Vigna angularis*) is an annual plant belonging to dicotyledonous Fabaceae family *Vigna* spp., which is the second most important pulse crops after beans. It is known that red bean is rich in vitamin B1, and when mixed with rice to make rice, it supplements vitamins that are scarce in rice, while being effective not only for the beriberi but also for the recovery of fatigue. The saponin contained in red beans has the effect of helping the evacuation with fibers, releasing poisons, promoting defecation, cleansing the intestines, and improving kidney disease or hangover (Korean Journal of Food Science and Technology, 42(6): 693-698, 2010). In addition, red bean has been reported to have such effects as anti-oxidant (Journal of Food Lipids 11(4): 278-286, 2004), anti-diabetic (Bioscience, Biotechnology, and Biochemistry, 68(12): 24212426, 2004), anti-bacterials (Phytotherapy Research 20(2): 162164, 2006), and whitening (International Journal of Molecular Sciences, 12(10): 7048-7058, 2011), but there has been no report on its efficacy associated with improving muscular function.

Accordingly, the present inventors have sought to develop plant extract-derived therapeutic agents for treating diseases associated with a decrease in muscle function such as muscle atrophy. As a result, the present inventors have confirmed that the extract of red bean or a leguminous plant can increase protein expression and phosphorylation level associated with muscle protein synthesis and muscle mass increase in muscle cells, and that the red bean or red bean extract according to the present invention can be used as an active ingredient of a composition for preventing or treating muscle disorders or for improving muscular function, completing the present invention.

DETAILED DESCRIPTION OF THE INVENTION

Technical Problem

Accordingly, the inventors of the present invention have searched for a natural substance that can be safely applied to improve muscular function or enhance exercise performance, and as a result, have confirmed that red bean possesses an activity of improving muscular function or enhancing exercise performance.

Thus, an aspect of the present invention is to provide a composition for treating a muscle disorder or enhancing exercise performance comprising an extract of red bean (*Vigna angularis*) as an active ingredient.

Another aspect of the present invention is to provide a composition for treating a muscle disorder or enhancing exercise performance comprising a red bean-derived protein or peptide as an active ingredient.

Still another aspect of the present invention is to provide a composition for improving muscular function comprising an extract of red bean (*Vigna angularis*) as an active ingredient.

Another aspect of the present invention is to provide a composition for improving muscular function comprising a red bean-derived protein or peptide as an active ingredient.

Technical Solution

According to are aspect of the present invention, there is provided a pharmaceutical composition for treating a muscle disorder or enhancing exercise performance comprising an extract of red bean (*Vigna angularis*) as an active ingredient.

According to another aspect of the present invention, there is provided a pharmaceutical composition for treating a muscle disorder or enhancing exercise performance comprising a red bean-derived protein or peptide as an active ingredient.

According to are aspect of the present invention, there is provided a composition for improving muscular function comprising an extract of red bean (*Vigna angularis*) as an active ingredient.

According to another aspect of the present invention, there is provided a composition for improving muscular function comprising a red bean-derived protein or peptide as an active ingredient.

Advantageous Effect

Accordingly, the present invention provides a composition for preventing or treating a muscle disorder, improving muscular function, or enhancing exercise performance comprising an extract of red bean, red bean-derived protein or red bean-derived peptide as an active ingredient.

The extract of red bean according to the present invention promotes mRNA transcription level and protein activity of factors involved in muscular function, muscle mass regulation or muscle cells differentiation in muscle cells, thereby leading to the improvement of muscular function or exercise performance due to increase in muscle mass, while it can exhibit an effect of preventing, treating or improving decreased exercise performance, decreased muscular function, muscle loss and the like caused by various diseases. Also, since the extract of red bean, red bean-derived protein and red bean-derived peptide according to the present invention are natural substances and do not cause any adverse side effects in the body, therefore, it can be effectively used as an ingredient for medicines, foods and the like.

BRIEF DESCRIPTION OF DRAWINGS/FIGURES

BEST MODE FOR CARRYING OUT THE INVENTION

Figure 1:
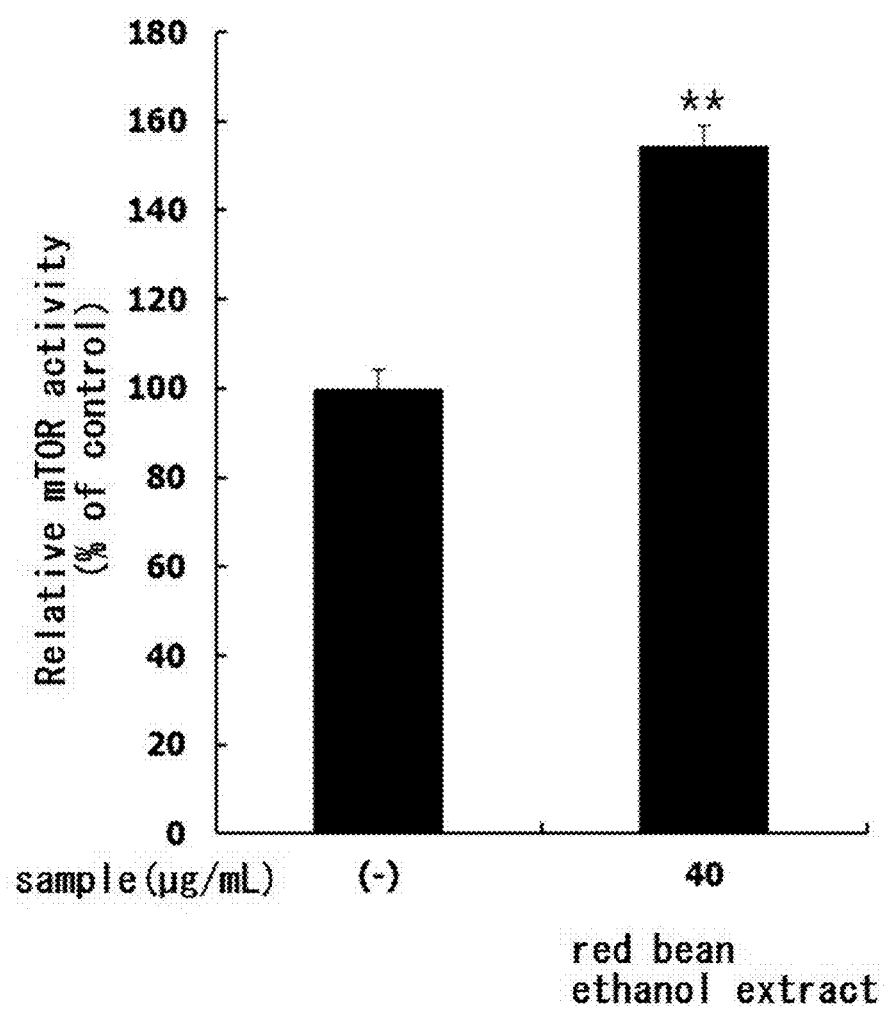
FIG. 1 shows the results of measuring an activity of mTOR after treatment with the ethanol extract red bean in L6 muscle cells.

Hereinafter, the present invention will be described in detail.

The present invention provides a pharmaceutical composition for treating a muscle disorder or enhancing exercise performance comprising an extract of red bean (*Vigna angularis*) as an active ingredient.

As used herein, the term 'red bean (*Vigna angularis*)' refers to a dried form of the seeds of red bean (*V. angularis* W. F. Wight), black bean (*V. angularis* var. *Angularis*) or other plants, belonging to the genus *Vigna* spp. of Fabaceae, while being used alone or in combination.

As used herein, the term 'an extract of red bean' means an extract obtained by extracting red beans. The method for producing red bean extract comprise extracting red bean with at least one solvent selected from the group consisting of water, $C_1$ to $C_6$ organic solvent, subcritical fluid and supercritical fluid. More specifically, the solvent may be at least one selected from the group consisting of alcohols having 1 to 6 carbon atoms, acetone, ether, benzene, chloroform, ethyl acetate, methylene chloride, hexane, cyclohexane and petroleum ether.

More specifically, the extract is preferably, but not limited to, one manufactured by a process comprising the steps of:
1) extracting red bean with an extraction solvent;
2) filtering the extract of step 1); and
3) concentrating the filtered extract of step 2) under reduced pressure followed by drying.

In the above method, the red beans of step 1) may include, without being limited to cultivated or commercially available ones.

In the above method, as an extraction method of red bean extract, conventional methods in the art such as filtration, hot water extraction, immersion extraction, reflux cooling extraction, ultrasonic extraction, ultra-high pressure extraction and subcritical extraction can be used. Regarding the extraction method, when performing the ultra-high pressure extraction, it is preferable to perform extraction at a pressure of 100 to 500 MPa.

In the above method, the concentration under reduced pressure in step 3) is preferable to use, but is not limited to, a vacuum decompression concentrator or a vacuum rotary evaporator. Also, drying may preferably include drying under reduced pressure, vacuum drying, boiling drying, spray drying or freeze drying, but is not limited thereto.

Also, the present invention provides a pharmaceutical composition for treating a muscle disorder or enhancing exercise performance comprising a red bean-derived protein or peptide as an active ingredient.

As used herein, the term 'red bean-derived protein' may be obtained by the following steps i) to v):
i) crushing a dried red bean, followed by extraction with hexane as a solvent;
ii) removing the hexane extract obtained in step i), and adding water to a residue, which is left at a pH of 7.0 to 10.0;
iii) obtaining a supernatant by centrifuging the residue solution left in step ii);
iv) leaving the supernatant obtained in step iii) at pH 2.0 to 6.0; and
v) centrifuging the supernatant left in step iv) to obtain a precipitate as a red bean-derived protein.

As used herein, the term 'red bean-derived peptide' means a red bean protein isolated from red bean by treating a protein hydrolase. Specifically, the red bean-derived peptide can be obtained by the following process steps i) to vii):
i) crushing a dried red bean, followed by extraction with hexane as a solvent;
ii) removing the hexane extract obtained in step i), and adding water to a residue, which is left at a pH of 7.0 to 10.0;
iii) obtaining a supernatant by centrifuging the residue solution left in step ii);
iv) leaving the supernatant obtained in step iii) at pH 2.0 to 6.0;
v) centrifuging the supernatant left in step iv) to obtain a precipitate as a red bean-derived protein;
vi) adding a hydrolase to the red bean-derived protein obtained in step v) for an enzyme reaction, followed by filtering to remove a precipitate; and
vii) lyophilizing a filtrate in which the precipitate is removed in step vi), so as to obtaining a peptide.

As used herein, the term 'hydrolase' is at least one protease selected from the group consisting of Alcalase, Flavourzyme, Neutrase, Protamex and Protease-NP.

As used herein, the term 'muscle disorder' is a muscle disorder caused by a decrease in muscle function, muscle wasting or muscle degeneration, and is preferably a disease reported in the art. The muscle wasting or muscle degeneration is caused by genetic factors, acquired factors, aging and the like. The muscle wasting is characterized by gradual loss of muscle mass, weakness and degeneration of muscles, especially skeletal muscle or voluntary muscle and cardiac muscle. Examples of diseases associated therewith may include atony, muscular atrophy, muscular dystrophy, muscle degeneration, myasthenia, cachexia and sarcopenia, and the like. The composition of the present invention has an effect of increasing muscle mass, while the kind of muscle is not limited.

As used herein, the term 'muscle' refers to sinews, muscles, and tendons in a comprehensive sense. The term 'muscular function' or 'muscle function' refers to the ability of the muscle to exert a force by its contraction, while it includes muscle strength to exert maximum contraction force to overcome resistance; muscle endurance which is the ability of a muscle to repeat how long or how many times it can contract and relax on a given weight; and muscle agility which is the ability of a muscle to exert a strong force in a short period of time. The muscle function is proportional to muscle mass. The expression 'improving muscular function' means that the muscular function is improved in a more preferable direction.

As used herein, the term 'exercise performance' refers to indicate the degree of body movements in theirs of speed, strength, accuracy, duration and skillfulness, when body movements in daily life or sports are divided into running, jumping, throwing, swimming, and the like while being defined by such factors as muscular strength, agility, and endurance. The expression 'enhancing exercise performance' refers to improving or enhancing exercise performance.

When the composition of the present invention is a pharmaceutical composition for enhancing exercise performance, it can be used for prevention or treatment of diseases due to degeneration of exercise ability. Examples of such diseases include degenerative disease, mitochondrial disorder, endurance dysfunction, agility dysfunction, lethargy, muscle loss, depression, and the like. The composition of the present invention has an effect of enhancing exercise performance and does not limit the type and kind of exercise.

In the case of a pharmaceutical composition for improving muscle function according to the present invention, it can be used for prevention or treatment of muscle diseases due to muscle wasting or degeneration. The muscle wasting or degeneration are caused by genetic factors, acquired factors, aging, etc. The muscle wasting is characterized by gradual loss of muscle mass, weakness and degeneration of muscles, especially skeletal or voluntary muscles and cardiac muscles. Examples of diseases associated therewith may include atony, muscular atrophy, muscular dystrophy, muscle degeneration, myasthenia, cachexia and sarcopenia, and the like. The composition of the present invention has an effect of increasing muscle mass, and the kind of muscle is not limited.

In the case of a pharmaceutical composition for enhancing exercise performance according to the present invention, it can be used for prevention or treatment of diseases caused by exercise ability degeneration. Examples of diseases associated therewith mitochondrial disorders, endurance dysfunction, agility dysfunction, lethargy, muscle loss and depression. The composition of the present invention has an effect of enhancing exercise performance, and does not limit the type and kind of exercise.

The pharmaceutical composition of the present invention may further contain a pharmaceutically acceptable carrier. Examples of the pharmaceutically acceptable carrier may further include a carrier for oral administration or a carrier for parenteral administration. The carrier for oral administration may include lactose, starch, a cellulose derivative, magnesium stearate, stearic acid, and the like. The carrier for parenteral administration may include water, proper oil, a saline solution, aqueous glucose, glycol, and the like. In addition, the carrier may further include a stabilizer and a preservative. Suitable examples of the stabilizer include an antioxidant, such as sodium hydrogen sulfite, sodium sulfite, or ascorbic acid. Suitable examples of the preservative include benzalkonium chloride, methyl- or propyl-paraben, and chlorobutanol. Other pharmaceutically acceptable carriers may be referenced in the following literature (Remington's Pharmaceutical Sciences, 19th ed., Mack Publishing Company, Easton, Pa., 1995).

The pharmaceutical composition of the present invention can be administered to mammals including humans by any method. For example, it can be administered orally or parenterally, and parental administration may be, but is not limited to, intravenous, intramuscular, intra-arterial, intramedullary, intradural, intracardiac, transdermal, subcutaneous, intraperitoneal, intranasal, intestinal, topical, sublingual, or rectal administration.

The pharmaceutical composition of the present invention may be formulated as a preparation for oral administration or parental administration according to the route of administration as described above. The composition according to the present invention may be formulated by using at least one buffer (for example, a saline solution or PBS), an antioxidant, a bacteriostat, a chelating agent (for example, EDTA or glutathione), a filler, an extender, a binder, an adjuvant (for example, aluminum hydroxide), a suspending agent, a thickener, a wetting agent, a disintegrant, or a surfactant, a diluting agent, or an excipient.

A solid preparation for oral administration includes a tablet, a pill, a powder, granules, a liquid, a gel, syrup, slurry, a suspension, or a capsule, and such a solid preparation may be manufactured by mixing, with the pharmaceutical composition of the present invention, at least one excipient, such as starch (including corn starch, wheat starch, rice starch, and potato starch), calcium carbonate, sucrose, lactose, dextrose, sorbitol, mannitol, xylitol, erythritol maltitol, cellulose, methylcellulose, sodium carboxymethyl cellulose, hydroxypropylmethyl-cellulose, or gelatin. For example, a tablet or a sugar-coated tablet may be obtained by mixing an active ingredient with a solid excipient, pulverizing the mixture, adding a suitable adjuvant thereto, and then processing the mixture into a granule mixture.

In addition to simple excipients, lubricants such as magnesium stearate and talc may be used. A liquid preparation for oral administration corresponds to a suspending agent, a liquid for internal use, an emulsion, a syrup, and the like, and may include, in addition to water or liquid paraffin as a simple diluent, several excipients, for example, a wetting agent, a sweetening agent, an aroma, and a preservative. In some cases, cross-linked polyvinyl pyrrolidone, agar, alginic acid, or sodium alginate may be added as a disintegrant, and an anti-coagulant, a lubricant, a wetting agent, a flavoring agent, an emulsifier, a preservative and the like may be further added.

As for the parenteral administration, the pharmaceutical composition of the present invention may be formulated, together with a suitable parenteral carrier, in a dosage form of an injection, an agent or preparation for transdermal administration, and a nasal inhalant, by a method known in the art. The injection needs to be essentially sterilized, and needs to be protected from the contamination of microorganisms, such as bacteria and fungus. Examples of the suitable carrier for the injection may include, but are not limited to, solvents or dispersion media, including water, ethanol, polyols (e. g., glycerol, propylene glycol, liquid polyethylene glycol, etc.), mixtures thereof, and/or vegetable oils. More preferably, Hanks' solution, Ringer's solution, phosphate buffered saline (PBS) or sterile water for injection containing triethanolamine, or an isotonic solution (such as 10% ethanol, 40% propylene glycol, or 5% dextrose) may be used as a suitable carrier. In order to protect the injection from microbial contamination, the injection may further contain various antibiotic and antifungal agents, such as paraben, chlorobutanol, phenol sorbic acid, and thimerosal. In most cases, the injection may further contain an isotonic agent, such as sugar or sodium chloride.

The form of the transdermal agent or preparation includes ointment, cream, lotion, gel, solution for external application, paste, liniment, and aerosol. The term "transdermal administration" means the delivery of an effective amount of an active ingredient, contained in the pharmaceutical composition, into the skin through the topical administration to the skin.

In the case of an inhalant, the compound used according to the invention may be conveniently delivered in the form of an aerosol spray from a pressurized pack or a sprayer, using a suitable propellant, for example, dichlorofluoromethane, trichlorofluoromethane, dichlorotetrafluoroethane, carbon dioxide, or other suitable gas. In the case of a pressurized aerosol, the dosage unit may be determined by providing a valve that delivers a measured quantity. For example, a gelatin capsule and a cartridge used in an inhaler or an insufflator may be formulated to contain a compound, and a powder mixture of proper powder materials, such as lactose or starch. Formulations for parenteral administration are described in the literature well known in the pharmaceutical chemistry (Remington's Pharmaceutical Science, 15th Edition, 1975. Mack Publishing Company, Easton, Pa. 18042, Chapter 87: Blaug, Seymour).

When containing red bean extract, red bean protein, red bean peptide in an effective amount, the pharmaceutical composition of the present invention can provide preferable effects of improving muscular function or enhancing exercise performance. As used herein, the term "effective amount" refers to an amount that exhibits a greater response than a negative control, and preferably an amount sufficient to improve muscle function or enhance exercise performance. The pharmaceutical composition of the present invention may contain 0.01-99.99% of red bean extract, red bean protein or red bean peptide and a remainder amount of a pharmaceutical acceptable carrier. The effective amount of red bean extract, red bean protein or red bean peptide contained in the pharmaceutical composition of the present invention may vary according to a formulation into which the composition is produced.

A total effective amount of the pharmaceutical composition according to the present invention may be administered to a patient in a single dose, or may be administered in multiple doses for a long period of time by a fractionated treatment protocol. In the pharmaceutical composition of the present invention, the content of the active ingredient may vary depending on the severity of a disease. When administered parenterally, it is administered in an amount of preferably 0.01 to 50 mg, more preferably 0.1 to 30 mg per kg of body weight a day on the basis of red bean extract, red bean protein or red bean peptide, and when administered orally, it may be administered once or divided into multiple doses so as to be administered in an amount of preferably 0.01 to 100 mg, more preferably 0.01 to 10 mg per kg of body weight a day on the basis of red bean extract, red bean protein or red bean peptide have. However, as for the dosage of red bean extract, red bean protein or red bean peptide, while an effective dose thereof is determined in consideration of various factors, such as route of administration, number of times of treatment, patient's age, body weight, health condition, and sex, severity of disease, food, and excretion rate, a person skilled in the art could determine a proper effective amount of the red bean extract, red bean protein or red bean peptide according to a particular use for improving muscular function or for enhancing exercise performance. The pharmaceutical composition according to the present invention is not particularly limited to its dosage form, route of administration, and administration method thereof as long as it shows the effects of the present invention.

The pharmaceutical composition of the present invention may be used alone or in combination with other methods employing surgery, radiation therapy, hormone therapy, chemical therapy, or a biological response controller.

The pharmaceutical composition of the present invention may be provided in a dosage form of an externally applied preparation containing, as an active ingredient, red bean extract, red bean protein or red bean peptide.

The pharmaceutical composition of the present invention, when used as an externally-applied preparation, may further contain an adjuvant that is commonly used in the field of dermatology, for example, a fatty substance, an organic solvent, a solubilizing agent, a concentrating agent, a gelling agent, a softening agent, an antioxidant, a suspending agent, a stabilizer, a forming agent, an aroma, a surfactant, water, an ionic or non-ionic emulsifier, a filler, a sequestering agent, a chelating agent, a preservative, vitamins, a blocker, a wetting agent, essential oil, a dye, a pigment, a hydrophilic or lipophilic activator, a lipid vesicle, or any other ingredient conventionally used in an externally-applied dermal preparation. In addition, the above ingredients may be introduced in amounts that are generally used in cosmetology.

The pharmaceutical composition of the present invention, when provided as an externally-applied preparation for skin, may be in a form of ointment, a patch, gel, cream, or aerosol, but is not limited thereto.

Also, the present invention provides a food composition for improving muscular function or enhancing exercise performance.

When the food composition of the present invention is a food composition for improving muscular function, it can be used for prevention or improvement of diseases reported in the art as muscular disorder caused by a decrease in muscular function, muscle wasting or muscle degeneration. The muscle wasting or muscle degeneration is caused by genetic factors, acquired factors, aging, and the like while the muscle wasting is characterized by gradual loss of muscle mass, weakness and degeneration of muscles, especially skeletal or voluntary muscles and cardiac muscles. Examples of diseases associated therewith may include atony, muscular atrophy, muscular dystrophy, muscle degeneration, myasthenia, cachexia and sarcopenia, and the like. The composition of the present invention has an effect of increasing muscle mass, and the kind of muscle is not limited. The muscular function is proportional to the muscle mass, while the expression 'improving muscular function' means that the muscular function is improved in a favorable manner.

When the food composition of the present invention is a food composition for enhancing exercise performance, it can be used for prevention or treatment of diseases caused by degeneration of exercise ability. Examples of such diseases include degenerative disease, mitochondrial disorders, endurance dysfunction, agility dysfunction, lethargy, muscle loss, depression, and the like. The composition of the present invention has an effect of enhancing exercise performance, while the type and kind of exercise are not limited.

The food composition of the present invention encompasses all food types including a functional food, a nutritional supplement, a health food, a food additive, and an animal feed, and the food composition are taken by humans or animals including livestocks. The above types of food composition may be manufactured in various forms according to conventional methods known in the art.

The above types of food composition may be manufactured in various forms according to the conventional methods known in the art. The food composition may be manufactured by adding the red bean extract and red bean peptide to general food including, but is not limited to, beverages (including alcoholic beverages), fruits and processed foods thereof (e.g., canned fruit, bottled food, jam, marmalade, etc.), fishes, meats and processed products thereof (e.g., ham, sausage, corned beef, etc.), breads, noodles (e.g., udong, buckwheat noodles, ramen, spaghetti, macaroni, etc.), fruit juices, a variety of drinks, cookies, syrups, dairy products (e.g., butter, cheese, etc.), edible vegetable oils, margarine, vegetable proteins, retort foods, frozen foods, and various seasonings (e.g., soybean paste, soybean sauce, sauces, etc.). Alternatively, a nutritional supplement may be manufactured by adding the red bean extract, red bean protein or red bean peptide to a capsule, tablet, pill, or the like, but is not limited thereto. As for health functional food, the red bean extract may be, for example, taken by liquefaction, granulation, encapsulation, and powdering such that the red bean extract itself can be drunk (as a health drink) in the form of tea, juice, and drink, but is not limited thereto. In addition, the red bean extract, red bean protein or red bean peptide may be manufactured in the form of a powder or a concentrate for the use as a form of a food additive. In addition, the red bean extract, red bean protein or red bean peptide may be manufactured in the form of a composition by mixing with an active ingredient that is known to have an effect of improving muscular function or for enhancing exercise performance.

When the food composition for improving muscular function or for enhancing exercise performance of the present invention is used as a health drink composition, it may contain, as additive ingredients, a plurality of flavoring agents or natural carbohydrates like in ordinary drinks. The foregoing carbohydrates may be monosaccharides, such as glucose and fructose; disaccharides such as maltose and sucrose; polysaccharides such as dextrin and cyclodextrin; and sugar alcohols, such as xylitol, sorbitol, and erythritol. The sweetening agent may include natural sweetening agents, such as thaumatin and *stevia* extracts; and synthetic sweetening agents, such as saccharin and aspartame. The proportion of the natural carbohydrate is generally about 0.01-0.04 g, and preferably about 0.02-0.03 g per 100 mL of the composition of the present invention.

Red bean extract, red bean protein or red bean peptide may be contained as an active ingredient of a food composition for improving muscular function or for enhancing exercise performance, and the amount thereof is an amount sufficient to obtain an effect of improving muscular function or enhancing exercise performance, and is not particularly limited. However, the content thereof is preferably 0.01-100 wt % relative to a total weight of the entire composition. The food composition of the present invention can be manufactured by mixing red bean extract with another active ingredient that is known to have an effect of improving muscular function or enhancing exercise performance.

Furthermore, the health food of the present invention may contain various nutrients, vitamins, electrolytes, flavoring agents, colorants, pectic acid and salts thereof, alginic acid and salts thereof, organic acids, protective colloid thickeners, pH adjusters, stabilizers, stabilizing agents, preservatives, glycerin, alcohols, or carbonating agents. In addition, the health food of the present invention may contain pulps for manufacturing natural fruit juice, fruit juice drink, and vegetable drink. These ingredients may be used independently or in mixture. The proportion of such an additive is not greatly important, but is generally selected within a range of 0.01-0.1 parts by weight relative to 100 parts by weight of the composition of the present invention.

MODE FOR CARRYING OUT INVENTION

Hereinafter, the present invention will be described in more detail with reference to examples, experimental examples and manufacturing examples. However, the following examples, experimental examples and preparation examples are illustrative of the present invention, and the present invention is not limited to the following examples, experimental examples and manufacturing examples.

Example 1: Preparation of Red Bean Extract 1-1. Preparation of Red Bean Methanol Extract Dried red beans (*Vigna angularis* W. F. Wight) were pulverized with a mixer, and 100 g of the pulverized red bean powder was immersed in 1 L of 100% methanol, allowed to stand at room temperature for 24 hours, and the process of obtaining the extract was repeated 3 times. The obtained extract was subjected to filtration under reduced pressure with Whatman No. 2 filter paper, and the filtered extract was concentrated with a vacuum rotary condenser to obtain red bean methanol extract from which solvent components were removed.

1-2. Preparation of Red Bean Ethanol Extract

Dried red beans (*V. angularis* W. F. Wight) were pulverized with a mixer, and 100 g of the pulverized red bean powder was immersed in 1 L of 100%, 70%, 50% or 30% ethanol, respectively, allowed to stand at room temperature for 24 hours, and the process of obtaining the extract was repeated 3 times. The obtained extract was subjected to filtration under reduced pressure with Whatman No. 2 filter paper, and the filtered extract was concentrated with a vacuum rotary condenser to obtain red bean ethanol extract from which solvent components were removed.

1-3. Preparation of Red Bean Ethyl Acetate Extract

Dried red beans (*V. angularis* W. F. Wight) were pulverized with a mixer, and 100 g of the pulverized red bean powder was immersed in 1 L of 100% ethyl acetate, allowed to stand at room temperature for 24 hours, and the process of obtaining the extract was repeated 3 times. The obtained extract was subjected to filtration under reduced pressure with Whatman No. 2 filter paper, and the filtered extract was concentrated with a vacuum rotary condenser to obtain red bean ethyl acetate extract from which solvent components were removed.

1-4. Preparation of Red Bean Hexane Extract

Dried red beans (*V. angularis* W. F. Wight) were pulverized with a mixer, and 100 g of the pulverized red bean powder was immersed in 1 L of 100% hexane, allowed to stand at room temperature for 24 hours, and the process of obtaining the extract was repeated 3 times. The obtained extract was subjected to filtration under reduced pressure with Whatman No. 2 filter paper, and the filtered extract was concentrated with a vacuum rotary condenser to obtain red bean hexane extract from which solvent components were removed.

1-5. Preparation of Red Bean Hot Water Extract

Dried red beans (*V. angularis* W. F. Wight) were pulverized with a mixer, and 100 g of the pulverized red bean powder was added to 1 L of water and stirred at 80° C. for 2 hours to obtain an extract. The obtained extract was subjected to filtration under reduced pressure with Whatman No. 2 filter paper, and the filtered extract was concentrated with a vacuum rotary condenser to obtain red bean methanol extract from which solvent components were removed.

1-6. Preparation of Red Bean Ultra-High Pressure Extract

Dried red beans (*V. angularis* W. F. Wight) were pulverized with a mixer, and then 76 mL of 18% ethanol was placed in a polyethylene pack, sealed, and then extracted using an ultra-high pressure extraction apparatus (Frescal MFP-7000; Mitsubishi Heavy Industries, Tokyo, Japan). As the ultra-high pressure extraction condition, the extraction pressure was set to 320 MPa and the extraction time was set to 5 minutes. The obtained extract was subjected to filtration under reduced pressure with Whatman No. 2 filter paper, and the filtered extract was concentrated with a vacuum rotary condenser to obtain red bean ultra-high pressure extract from which solvent components were removed.

1-7. Preparation of Red Bean Subcritical Extract

Dried red beans (*V. angularis* W. F. Wight) were pulverized with a mixer, and 50 g of pulverized red beans were placed in a subcritical extraction device (Biovan, Gyeonggi, Republic of Korea) with 1 L water and sealed. After sealing, the temperature of the reactor was raised to 200° C., and when the temperature of the reactor reached 200° C., the temperature was maintained for 20 minutes to extract. After 20 minutes, the extract was transferred to a storage tank to which cooling water was supplied, cooled rapidly to 30° C., and centrifuged at 3,600 rpm for 30 minutes to separate the floating residue and obtain a supernant. Using a freeze dryer (ilShin Lab Co. Ltd., Seoul, Republic of Korea), the solvent was completely removed to obtain red bean subcritical extracts.

Example 2: Separation of Red Bean-Derived Proteins and Peptides 2-1. Separation of Red Bean-Derived Protein The dried red beans (*V. angularis* W. F. Wight) were pulverized, and 1 kg of pulverized red beans was added to 1 L of hexane and extracted with stirring at room temperature for 4 hours. After removing the hexane extract, water was added to the residue and allowed to stand at pH 9, 25° C. for 30 minutes. The mixture was centrifuged at 6,000 rpm for 30 minutes to obtain a supernatant, and the supernatant was allowed to stand at pH 4.5, 25° C. for 30 minutes. And then centrifuged at 6,000 rpm for 30 minutes to obtain a precipitated protein. The precipitated protein was dissolved in water, and after neutralization, all of the water was removed by using a freeze dryer (ilShin Lab Co. Ltd., Seoul, Republic of Korea) to obtain separated red bean proteins.

2-2. Preparation of Red Bean Peptides by Treatment with Alcalase

The protease 1% alcalase (Novozymes, Bagsvaerd, Denmark) was added to the red bean protein obtained in Example 2-1, and enzyme reaction was performed at 50° C. for 6 hours. After 6 hours, the enzyme was inactivated at 90° C. for 20 minutes and the precipitate was removed by filtration through a filter paper of Watson number 2. Water was completely removed from the filtered liquid by using a freeze dryer (ilShin Lab Co. Ltd., Seoul, Republic of Korea) to obtain red bean peptides by alcalase treatment.

2-3. Preparation of Red Bean Peptide by Treatment with Flavourzyme

In the same manner as in Example 2-2, the flavourzyme (Novozymes) was treated in place of the alcalase to obtain the red bean peptide by flavourzyme treatment.

2-4. Preparation of Red Bean Peptide by Treatment with Neutrase

In the same manner as in Example 2-2, the neutrase (Novozymes) was treated in place of the alcalase to obtain the red bean peptide by neutrase treatment.

2-5. Preparation of Red Bean Peptide by Treatment with Protamex

In the same manner as in Example 2-2, the protamex (Novozymes) was treated in place of the alcalase to obtain the red bean peptide by protamex treatment.

2-6. Preparation of Red Bean Peptide by Treatment with Protease-NP

In the same manner as in Example 2-2, the Protease-NP (Bioland, Asan, Republic of Korea) was treated in place of the alcalase to obtain the red bean peptide by Protease-NP treatment.

Example 3: Preparation of Black Bean Extract 3-1. Preparation of Black Bean Methanol Extract Dried black beans (*V. angularis* var. *angularis*) were pulverized with a mixer, and 100 g of the pulverized black bean powder was immersed in 1 L of 100% methanol, allowed to stand at room temperature for 24 hours, and the process of obtaining the extract was repeated 3 times. The obtained extract was subjected to filtration under reduced pressure with Whatman No. 2 filter paper, and the filtered extract was concentrated with a vacuum rotary condenser to obtain black bean methanol extract from which solvent components were removed.

3-2. Preparation of Black Bean Ethanol Extract

Dried black beans (*V. angularis* var. *angularis*) were pulverized with a mixer, and 100 g of the pulverized black bean powder was immersed in 1 L of 100%, 70%, 50% or 30% ethanol, respectively, allowed to stand at room temperature for 24 hours, and the process of obtaining the extract was repeated 3 times. The obtained extract was subjected to filtration under reduced pressure with Whatman No. 2 filter paper, and the filtered extract was concentrated with a vacuum rotary condenser to obtain black bean ethanol extract from which solvent components were removed.

3-3. Preparation of Black Bean Ethyl Acetate Extract

Dried black beans (*V. angularis* var. *angularis*) were pulverized with a mixer, and 100 g of the pulverized black bean powder was immersed in 1 L of 100% ethyl acetate, allowed to stand at room temperature for 24 hours, and the process of obtaining the extract was repeated 3 times. The obtained extract was subjected to filtration under reduced pressure with Whatman No. 2 filter paper, and the filtered extract was concentrated with a vacuum rotary condenser to obtain black bean ethyl acetate extract from which solvent components were removed.

3-4. Preparation of Black Bean Hexane Extract

Dried black beans (*V. angularis* var. *angularis*) were pulverized with a mixer, and 100 g of the pulverized black bean powder was immersed in 1 L of 100% hexane, allowed to stand at room temperature for 24 hours, and the process of obtaining the extract was repeated 3 times. The obtained extract was subjected to filtration under reduced pressure with Whatman No. 2 filter paper, and the filtered extract was concentrated with a vacuum rotary condenser to obtain black bean hexane extract from which solvent components were removed.

3-5 Preparation of Black Bean Hot Water Extract

Dried black beans (*V. angularis* var. *angularis*) were pulverized with a mixer, and 100 g of the pulverized black bean powder was added to 1 L of water and stirred at 80° C. for 2 hours to obtain an extract. The obtained extract was subjected to filtration under reduced pressure with Whatman No. 2 filter paper, and the filtered extract was concentrated with a vacuum rotary condenser to obtain black bean methanol extract from which solvent components were removed.

3-6. Preparation of Black Bean Ultra-High Pressure Extract

Dried black beans (*V. angularis* var. *angularis*) were pulverized with a mixer, and then 76 mL of 18% ethanol was placed in a polyethylene pack, sealed, and then extracted using an ultra-high pressure extraction apparatus (Frescal MFP-7000; Mitsubishi Heavy Industries, Tokyo, Japan). As the ultra-high pressure extraction condition, the extraction pressure was set to 320 MPa and the extraction time was set to 5 minutes. The obtained extract was subjected to filtration under reduced pressure with Whatman No. 2 filter paper, and the filtered extract was concentrated with a vacuum rotary condenser to obtain black bean ultra-high pressure extract from which solvent components were removed.

3-7. Preparation of Black Bean Subcritical Extract

Dried black beans (*V. angularis* var. *angularis*) were pulverized with a mixer, and 50 g of pulverized black beans were placed in a subcritical extraction device (Biovan, Gyeonggi, Republic of Korea) with 1 L water and sealed. After sealing, the temperature of the reactor was raised to 200° C., and when the temperature of the reactor reached 200° C., the temperature was maintained for 20 minutes to extract. After 20 minutes, the extract was transferred to a storage tank to which cooling water was supplied, cooled rapidly to 30° C., and centrifuged at 3,600 rpm for 30 minutes to separate the floating residue and obtain a supernatant. Using a freeze dryer (ilShin Lab Co. Ltd., Seoul, Republic of Korea), the solvent was completely removed to obtain black bean subcritical extracts.

Example 4: Separation of Black Bean-Derived Proteins and Peptides 4-1. Separation of Black Bean-Derived Protein The dried black beans (*V. angularis* var. *angularis*) were pulverized, and 1 kg of pulverized black beans was added to 1 L of hexane and extracted with stirring at room temperature for 4 hours. After removing the hexane extract, water was added to the residue and allowed to stand at pH 9, 25° C. for 30 minutes. The mixture was centrifuged at 6,000 rpm for 30 minutes to obtain a supernatant, and the supernatant was allowed to stand at pH 4.5, 25° C. for 30 minutes. And then centrifuged at 6,000 rpm for 30 minutes to obtain a precipitated protein. The precipitated protein was dissolved in water, and after neutralization, all of the water was removed by using a freeze dryer (ilShin Lab Co. Ltd., Seoul, Republic of Korea) to obtain separated black bean protein.

4-2. Preparation of Black Bean Peptide by Treatment with Alcalase

The protease 1% alcalase (Novozymes, Bagsvaerd, Denmark) was added to the black bean protein obtained in Example 2-1, and enzyme reaction was performed at 50° C. for 6 hours. After 6 hours, the enzyme was inactivated at 90° C. for 20 minutes and the precipitate was removed by filtration through a filter paper of Watson number 2. The filtered liquid was completely removed by using a freeze dryer (ilShin Lab Co. Ltd., Seoul, Republic of Korea) to obtain black bean peptides by alcalase treatment.

4-3. Preparation of Black Bean Peptide by Treatment with Flavourzyme

In the same manner as in Example 4-2, the flavourzyme (Novozymes) was treated in place of the alcalase to obtain the black bean peptide by flavourzyme treatment.

4-4. Preparation of Black Bean Peptide by Treatment with Neutrase

In the same manner as in Example 4-2, the neutrase (Novozymes) was treated in place of the alcalase to obtain the black bean peptide by neutrase treatment.

4-5. Preparation of Black Bean Peptide by Treatment with Protamex

In the same manner as in Example 4-2, the protamex (Novozymes) was treated in place of the alcalase to obtain the black bean peptide by protamex treatment.

4-6. Preparation of Black Bean Peptide by Treatment with Protease-NP

In the same manner as in Example 4-2, the Protease-NP (Bioland, Asan, Republic of Korea) was treated in place of the alcalase to obtain the black bean peptide by Protease-NP treatment.

Experimental Example 1: Evaluation on Muscle Production Activity of Red Bean Ethanol Extract It is known that mTOR protein, when phosphorylated and activated, can induce protein activation involved in muscle protein synthesis and muscle mass increase in myocyte PI3K/Akt signaling pathway. Therefore, mTOR sandwich ELISA kit was used to confirm the activity of mTOR to determine the activity of the red bean ethanol extract in inducing muscle production.

The myoblast L6 cells (ATCC; Manassas, Va., USA) were inoculated on a 6-well plate with Dulbecco's modified Eagle's media (DMEM; Hyclone) containing 10% fetal bovine serum (FBS; Hyclone, Logan, Utah, USA) at a concentration of $1 \times 10^5$ cell/mL and cultured for 24 hours. After the culture, the medium in the wells was removed, and the medium was replaced with DMEM (Hyclone) containing 2% horse serum (HS; Hyclone), and the cells were further cultured for 6 days to differentiate L6 cells into myotube. Subsequently, red bean ethanol extract manufactured from 100% ethanol in Example 1-2 was treated with said cells at a concentration of 40 μg/mL and cultured for 12 hours. After the culture, the cells were lysed by treatment with cell lysis buffer. The proteins in the obtained cell lysate were quantified by the Bradford method (Bio-Rad Laboratories Inc., Hercules, Calif., USA), and quantified to a concentration of 1 mg/mL, 50 μL of the cell lysate was dispensed into microwell attached with anti-mTOR antibody, and incubated at 37° C. for 2 hours. After incubation, the cells were washed 4 times with washing buffer, treated with detection antibody, incubated at 37° C. for 1 hour, washed 4 times with washing buffer, horseradish peroxidase (HRP) conjugated secondary antibody was added and incubated at 37° C. for 30 min. Finally, after washing 4 times with wash buffer, TMB substrate was added to each well, incubated at 37° C. for 10 min, and TBM reaction was stopped by adding stop solution. Two minutes later, absorbance was measured at 450 nm and mTOR levels in myotube treated with the red bean ethanol extract were measured. The results are shown in FIG. 1.

As a result, as shown in FIG. 1, the activity of mTOR in L6 muscle cells was significantly increased (** $p<0.01$) by treatment with red bean ethanol extract. This suggests that the red bean ethanol extract of the present invention has an excellent ability to increase muscle production in muscle cells.

Experimental Example 2: Evaluation on mRNA Transcription Level of Muscle Protein Synthesis Factor of Red Bean Ethanol Extract The myoblast L6 cells (ATCC) were inoculated on a 6-well plate DMEM containing 10% FBS (Hyclone) at a concentration of $2 \times 10^5$ cell/mL and cultured. When the cell density reached about 80 to 85%, the medium in the wells was removed, and the medium was replaced with DMEM (Hyclone) containing 2% HS (Hyclone) to differentiate L6 cells into myotube. After 6 days, the medium was replaced with DMEM (Hyclone) in which 25, 50 or 40 μg/mL of red bean ethanol extract manufactured from 100% ethanol in Example 1-2 was exchanged and cultured for 24 hours. At this time, a group treated with 0.01% DMSO instead of the sample was used as a control group. After 24 hours, cells were harvested and lysed in NP-40 buffer (ELPIS-Biotech, Daejeon, Republic of Korea) containing protease inhibitor cocktail (Sigma-Aldrich St. Louis, Mo., USA) to obtain a cell lysate. The obtained cell lysate was centrifuged at 13,000 rpm for 10 minutes to obtain the supernatant. The protein concentration in the supernatant was quantitated with Bradford, and a constant concentration of the protein was heated for 5 minutes, developed on 10% SDS-PAGE gel, and intracellular proteins were separated by SDS-PAGE electrophoresis. The separated proteins were transferred to the nitrocellulose membrane. And then, anti-p-p70S6K antibody, anti-t-p70S6K antibody, anti-p-4EBP1 antibody, anti-t-4EBP1 antibody or anti-α-tubulin antibody (Cell Signaling Technology) was diluted with a ratio of 1:1000 to 2.5% bovine serum albumin (BSA), respectively, and the protein transferred to the nitrocellulose membrane as the primary antibody was reacted at room temperature for 20 hours. After the primary antibody was reacted, the nitrocellulose membrane was washed with Tris-buffer Saline Tween 20 (TBST) three times for 10 minutes. And then, HRP-conjugated secondary antibody (Bethyl Laboratories, Inc., Montgomery, TA, USA) recognizing the primary antibody was diluted to 1:5000 in 2.5% BSA (bioWORLD) and allowed to react with the nitrocellulose membrane at room temperature for 2 hours, and washed three times for 10 minutes using TBST. Protein bands were detected using ECL Western blot detection reagent (Amersham, Tokyo, Japan), the protein bands were identified using the G; BOX EF imaging system (Syngene, Cambridge, UK). The results are shown in FIG. 2.

Figure 2:
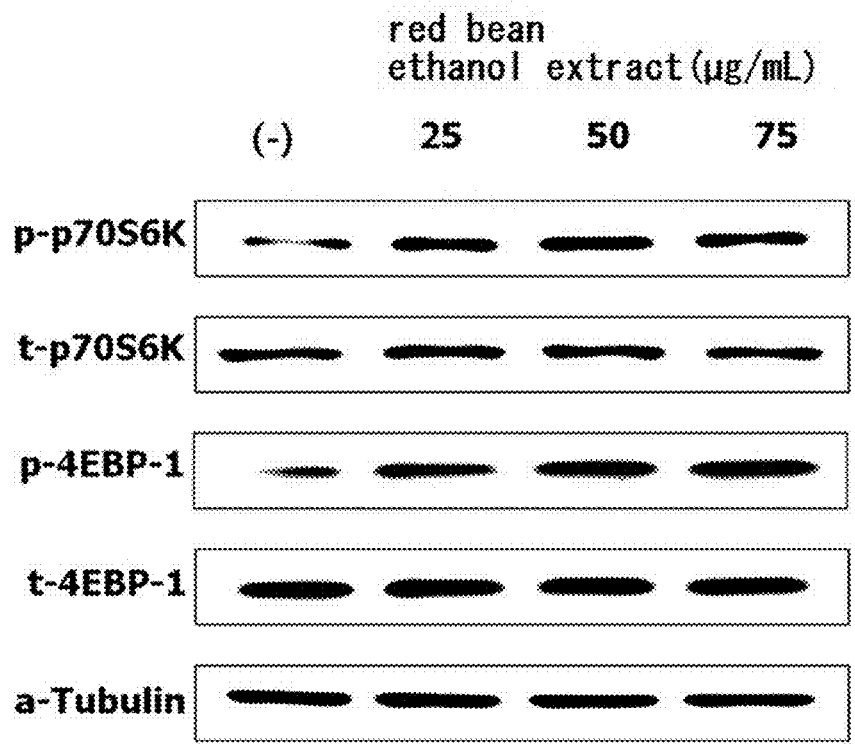
FIG. 2 shows the results of measuring the expression levels of p-p70S6K and p-4EBP1 proteins, which are mRNA translation-related biomarkers, after treatment with the ethanol extract red bean in L6 muscle cells.

As a result, as shown in FIG. 2, it was confirmed that the level of protein expression of p-p70S6K and p-4EBP1, which are involved in muscle protein synthesis, is increased by mRNA transcription in L6 muscle cells by treating the red bean ethanol extract. This means that the red bean ethanol extract of the present invention promotes the mRNA translation process of the relevant factors for muscle protein synthesis in muscle cells.

Experimental Example 3: Evaluation on the Inhibition of Muscle Protein Degradation of Red Bean Ethanol Extract The myoblast L6 cells (ATCC) were inoculated on a 6-well plate DMEM (Hyclone) containing 10% FBS (Hyclone) at a concentration of $2 \times 10^5$ cell/mL and cultured. When the cell density reached about 80 to 85%, the medium in the wells was removed, and the medium was replaced with DMEM (Hyclone) containing 2% HS (Hyclone) to differentiate L6 cells into myotube. Replacement with fresh medium was done once every 2 days, and the differentiation was carried out for a total of 6 days. After the differentiation, the red bean ethanol extract manufactured from 100% ethanol in the above Example 1-2 was dissolved at a concentration of 20 or 40 μg/mL in a DMEM medium containing 50 ng/mL of TNF-α, and treated onto the cells. Six hours later, total RNAs were isolated using TRIzol reagent (Takara, Osaka, Japan). The isolated total RNAs were quantified using nano drop (NanoDrop 1000; Thermo Fisher Scientific Inc., Waltham, Mass., USA). 16 μL of RNA was quantified, mixed with reverse transcriptase premix (Reverse Transcriptase Premix, ELPIS-Biotech), and synthesized by cDNA using PCR machine at 42° C. for 55 minutes and 70° C. for 15 minutes. A PCR sample was manufactured by mixing 4 μL of the synthesized cDNA, the forward and reverse primer pairs (Bioneer, Deajeon, Republic of Korea) of the sequences listed in Table 1, and the PCR premix (ELPIS-Biotech) and then PCR was performed by repeating 30 cycles of 95° C. for 30 seconds, 60° C. for 1 minute, and 72° C. for 1 minutes.

Figure 3:
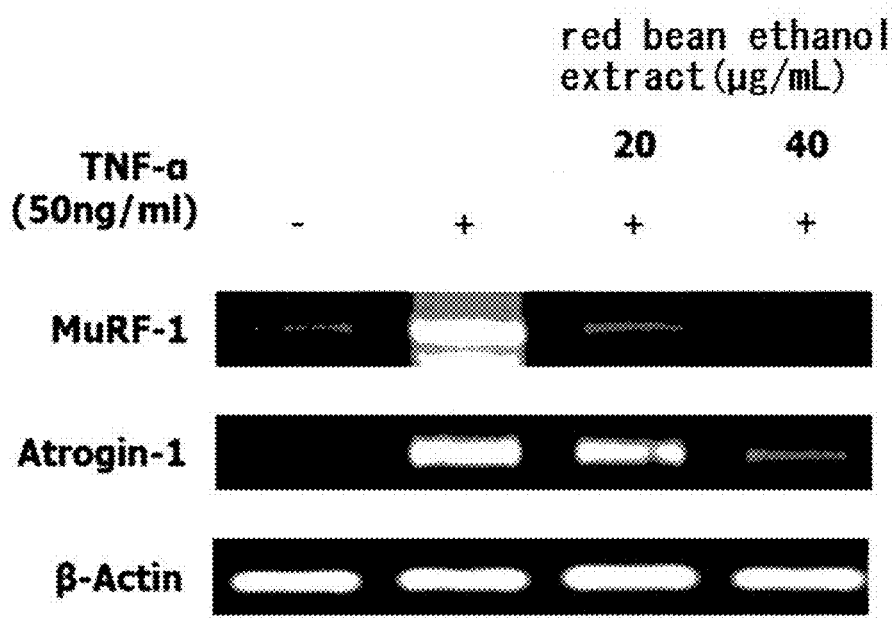
FIG. 3 shows the results of measuring mRNA expression levels of MuRF-1 and atrogin-1, which are biomarkers for the promotion of muscle protein degradation, after treatment with the ethanol extract red bean in L6 muscle cells.

The amplified cDNAs were separated by electrophoresis on 1.5% agarose gel and cDNA bands were confirmed using G; BOX EF imaging system (Syngene). The results are shown in FIG. 3.

TABLE 1

The primer sequences used for PCR in embodiments the present invention

| Amplified gene | Sequence name | SEQ ID NO: | Sequence | Direction |
|---|---|---|---|---|
| Atrogin-1 | Atrogin_F | SEQ ID NO: 1 | 5'-GTCCAGAGAG TCGGCAAGTC-3' | Forward |
|  | Atrogin_R | SEQ ID NO: 2 | 5'-GTCGGTGATC GTGAGACCTT-3' | Reverse |
| MuRF-1 | MuRF_F | SEQ ID NO: 3 | 5'-TCTACTCGGC CACAGGCGCT-3' | Forward |
|  | MuRF_R | SEQ ID NO: 4 | 5'-CTTGACAGCT CCCGCCGCAA-3' | Reverse |
| β-Actin | Actin_F | SEQ ID NO: 5 | 5'-CTGTGTGGATT GGTGGCTCTAT-3' | Forward |
|  | Actin_R | SEQ ID NO: 6 | 5'-GTGTAAAACGC AGCTCAGTAACA3' | Reverse |

As a result, as shown in FIG. 3, the mRNA expression of atrogin-1 and MuRF-1 mRNA was decreased in L6 muscle cells by treatment with red bean ethanol extract. This means that the red bean ethanol extract of the present invention has an excellent ability to inhibit muscle protein degradation in muscle cells.

Figure 4:
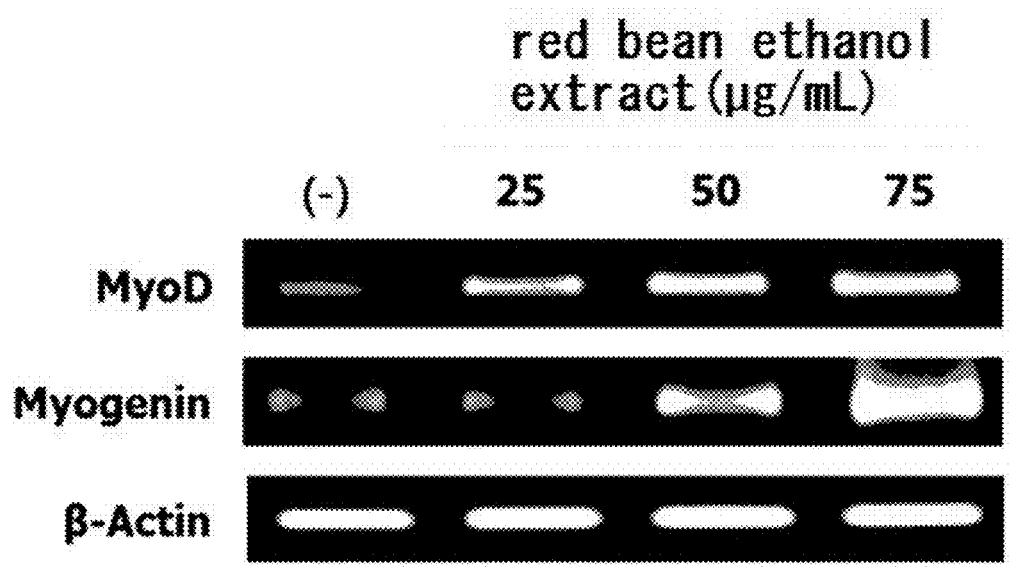
FIG. 4 shows the results of measuring mRNA expression levels of MyoD and myogenin, which are biomarkers of muscle differentiation, after treatment with the ethanol extract red bean in L6 muscle cells.

Experimental Example 4: Evaluation on the Activity of Red Bean Ethanol Extract in Promoting Muscle Differentiation The myoblast L6 cells (ATCC) were inoculated on a 6-well plate DMEM containing 10% FBS (Hyclone) at a concentration of $2 \times 10^5$ cell/mL and cultured. When the cell density reached about 80 to 85%, the medium in the wells was removed, and the red bean ethanol extract manufactured from 100% ethanol in Example 1-2 was dissolved in DMEM (Hyclone) containing 2% HS at a concentration of 25, 50 or 40 μg/mL, and treated with cells to induce differentiation into myotube. At this time, a group treated with 0.01% DMSO instead of the sample was used as a control group. This procedure was repeated three times for 2 days, for a total of 6 days, and then total RNAs were isolated using TRIzol reagent (Takara). The isolated RNAs were performed to cDNAs synthesis and PCR in the same manner as in Experimental Example 3 to confirm mRNA transcription levels of MyoD and myogenin. The sequence of primer (Bioneer) used for the PCR is as shown in Table 2 below. The amplified cDNA was separated by electrophoresis on 1.5% agarose gel and cDNA bands were confirmed using G; BOX EF imaging system (Syngene). The results are shown in FIG. 4.

TABLE 2

The primer sequences used for PCR in embodiments the present invention

| Amplified gene | Sequence name | SEQ ID NO: | Sequence | Direction |
|---|---|---|---|---|
| MyoD | MyoD_F | SEQ ID NO: 7 | 5'-GGATGGTGCCC CTGGGTCCT-3' | Forward |
|  | MyoD_R | SEQ ID NO: 8 | 5'-TGGCCTTCGCT GTGAGTCGC-3' | Reverse |
| Myogenin | Myogenin_F | SEQ ID NO: 9 | 5'-TGGGCTGCCAC AAGCCAGAC-3' | Forward |
|  | Myogenin_R | SEQ ID NO: 10 | 5'-CAGCCCAGCCA CTGGCATCA-3' | Reverse |
| β-Actin | Actin_F | SEQ ID NO: 5 | 5'-CTGTGTGGATT GGTGGCTCTAT-3' | Forward |
|  | Actin_R | SEQ ID NO: 6 | 5'-GTGTAAAACGC AGCTCAGTAACA3' | Reverse |

As a result, as shown in FIG. 4, the mRNA expression of MyoD and myogenin mRNA was increased in L6 muscle cells by treatment with red bean ethanol extract. This means that the red bean ethanol extract of the present invention has excellent ability to promote muscle differentiation in muscle cells.

Experimental Example 5: Muscle Production Activity of Red Bean Hot Water Extract In the same manner as in Experimental Example 1, the mTOR activity was evaluated by treating 40 μg/mL of the red bean hot water extract manufactured in Example 1-5. The results are shown in FIG. 5.

Figure 5:
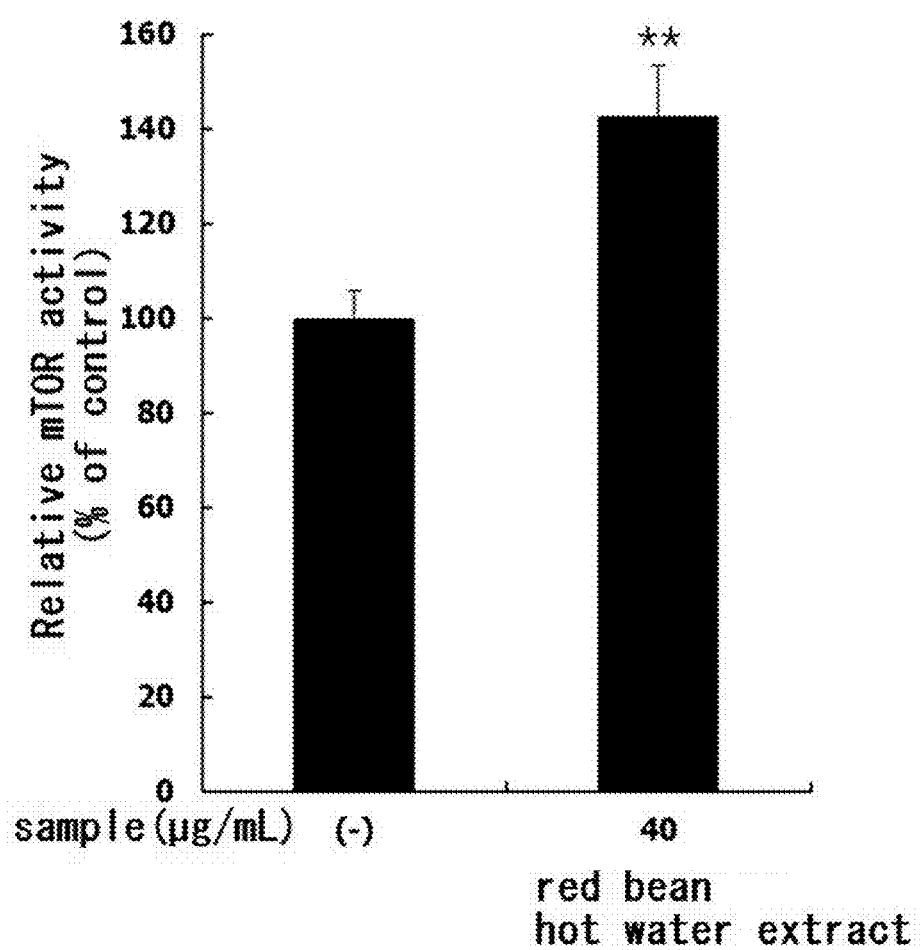
FIG. 5 shows the results of measuring an activity of mTOR after treatment with the hot water extract red bean in L6 muscle cells.

As shown in FIG. 5, the activity of mTOR in L6 muscle cells was significantly increased (** $p<0.01$) by treatment with red bean hot water extract. This means that the red bean hot water extract of the present invention has an excellent ability to increase muscle production in muscle cells.

Experimental Example 6: Muscle Production Activity of Red Bean Subcritical Extract In the same manner as in Experimental Example 1, the mTOR activity was evaluated by treating 5 μg/mL of the red bean subcritical extract manufactured in Example 1-7. The results are shown in FIG. 6.

Figure 6:
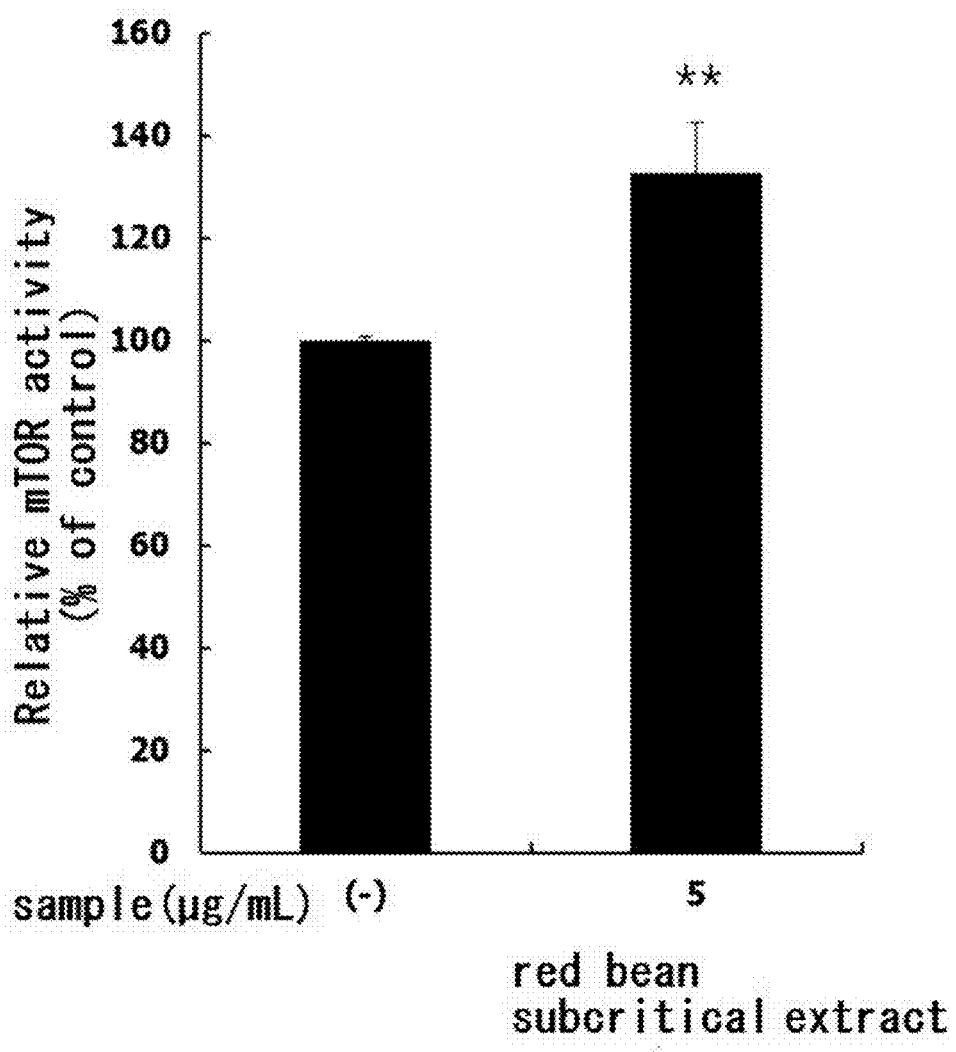
FIG. 6 shows the results of measuring an expression level of mTOR after treatment with the subcritical extract red bean in L6 muscle cells.

As shown in FIG. 6, the activity of mTOR in L6 muscle cells was significantly increased (** $p<0.01$) by treatment with red bean subcritical extract. This means that the red bean subcritical extract of the present invention has an excellent ability to increase muscle production in muscle cells.

Experimental Example 7: Muscle Production Activity of Red Bean Protein and Peptide In the same manner as in Experimental Example 1, the mTOR activity was evaluated by treating 40 μg/mL of the red bean protein and red bean peptide manufactured in Example 2-1, 2-4, 2-5, and 2-6, respectively. The results are shown in FIG. 7.

Figure 7:
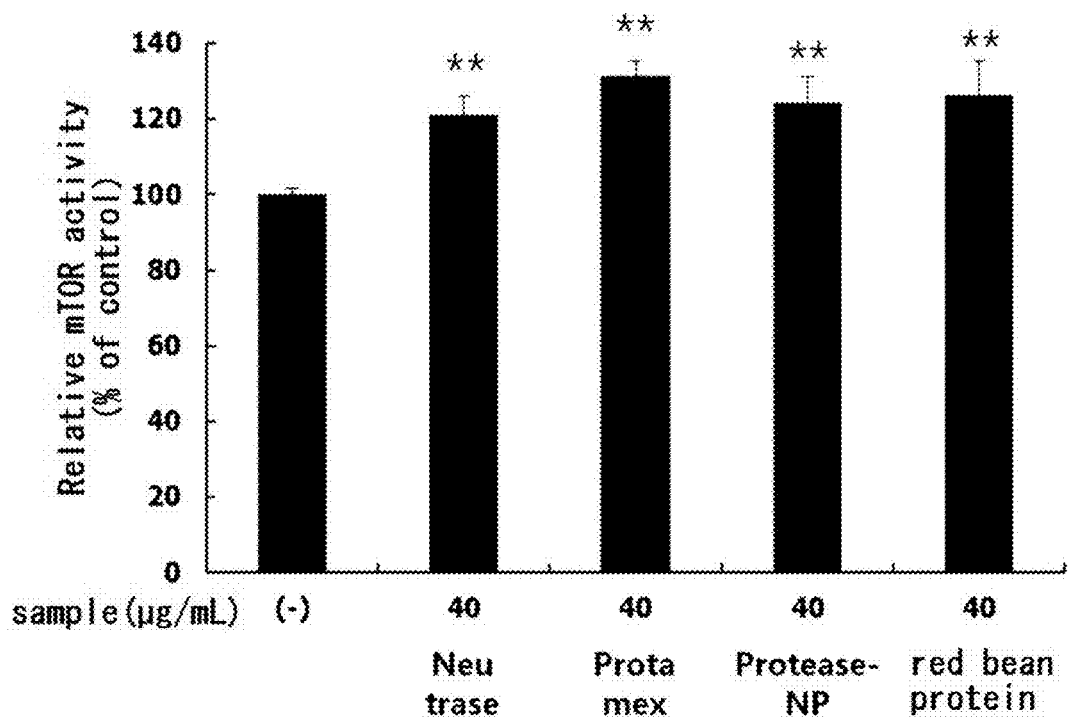
FIG. 7 shows the results of measuring an expression level of mTOR after treatment with red bean protein and red bean peptide by enzymatic reaction in L6 muscle cells, respectively.

As a result, as shown in FIG. 7, the activity of mTOR in L6 muscle cells was significantly increased (** $p<0.01$) by treatment with red bean protein and red bean peptide. This means that the red bean protein and red bean peptide of the present invention has an excellent ability to increase muscle production in muscle cells.

Experimental Example 8: mRNA Transcription-Promoting Activity of Red Bean Peptide In the same manner as in Experimental Example 2, the mTOR activity was evaluated by treating 50 or 100 μg/mL of the red bean peptide manufactured in Example 2-5. The results are shown in FIG. 8.

Figure 8:
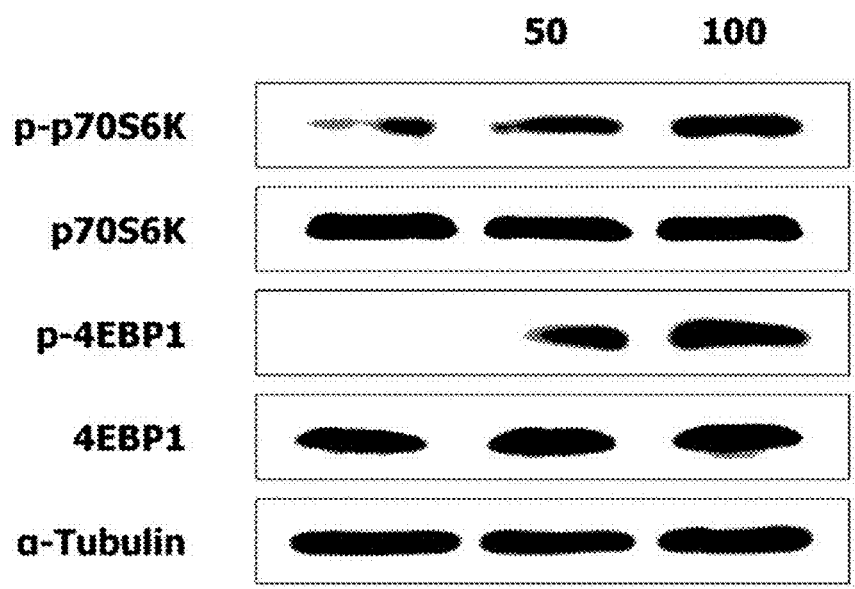
FIG. 8 shows the results of measuring p-p70S6K and p-4EBP1 proteins expression levels, which are mRNA translation-related biomarkers, after treatment with red bean peptide in L6 muscle cells.

As a result, as shown in FIG. 8, it was confirmed that the protein expression of p-p70S6K and p-4EBP1, which are involved in muscle protein synthesis, is increased through the mRNA transcription in L6 muscle cells by treating the red bean peptide. This means that the red bean peptide of the present invention promotes mRNA transcription for muscle protein synthesis in muscle cells.

Experimental Example 9: Muscle Differentiation-Promoting Activity of Red Bean Peptide The experiment was carried out in the same manner as in Experimental Example 4. Instead of the red bean ethanol extract, the red bean peptide manufactured in Example 2-5 was dissolved at a concentration of 50 or 100 μg/mL, and then treated with cells to induce differentiation into myotube. At this time, a group treated with 0.01% DMSO instead of the sample was used as a control group. The results are shown in FIG. 9.

Figure 9:
FIG. 9 shows the results of measuring mRNA expression levels of MyoD and myogenin, which are biomarkers of muscle differentiation, after treatment with red bean peptide in L6 muscle cells.
Figure 9:
Figure 9:

As a result, as shown in FIG. 9, MyoD and myogenin mRNA expression was increased in L6 muscle cells by treatment with red bean peptide. This means that the red bean peptide of the present invention is excellent in the ability to promote muscle differentiation in muscle cells.

Experimental Example 10: Muscle Production Activity of Black Bean Ethanol Extract In the same manner as in Experimental Example 1, mTOR activity was evaluated by treating 40 ug/mL of black bean ethanol extract manufactured from 100% ethanol in Example 3-2. The results are shown in FIG. 10.

Figure 10:
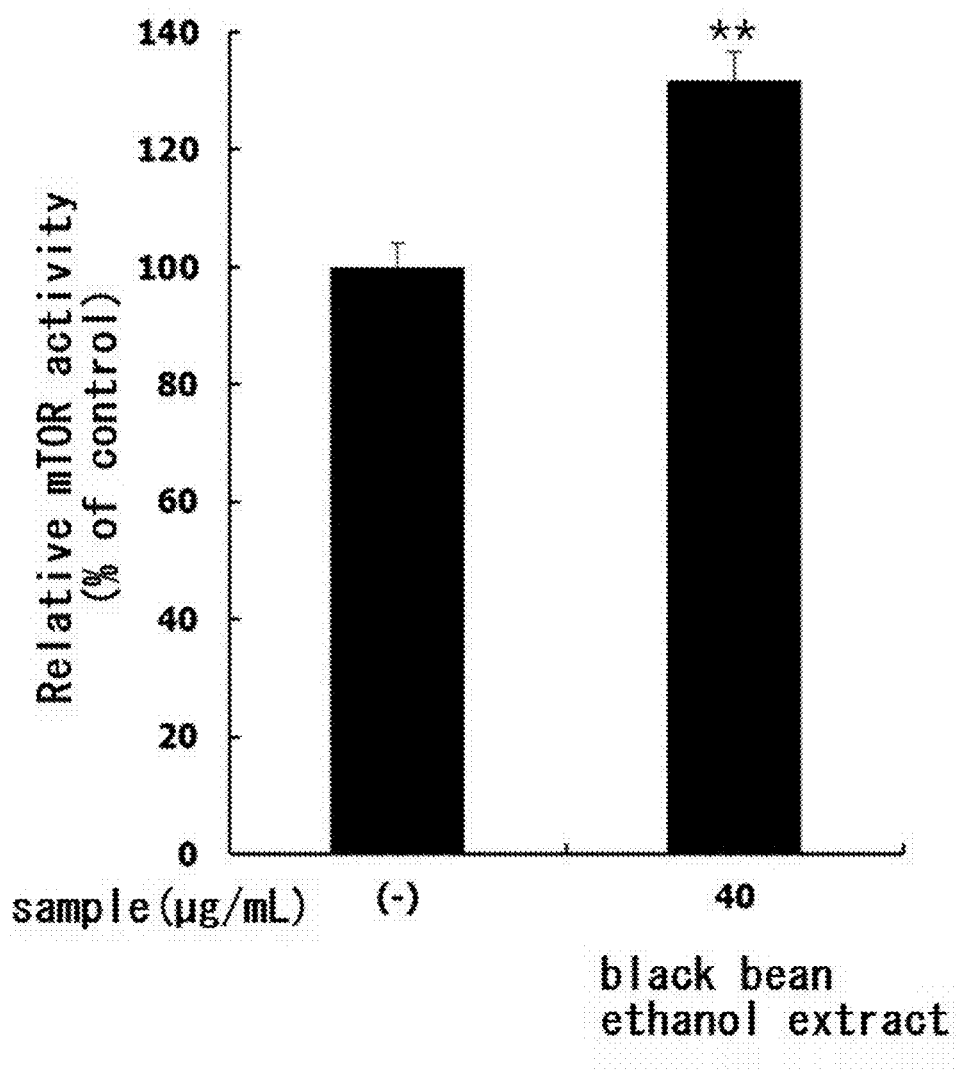
FIG. 10 shows the results of measuring an activity of mTOR after treatment with the ethanol extract black bean in L6 muscle cells.

As shown in FIG. 10, the activity of mTOR in L6 muscle cells was significantly increased (** $p<0.01$) by treatment with black bean ethanol extract. This means that the black bean ethanol extract of the present invention has an excellent ability to increase muscle production in muscle cells.

Experimental Example 11; Enhancement of Exercise Performance of Red Bean Ethanol Extract In order to evaluate the exercise performance of the red bean ethanol extract, PGC-1α activity was assayed by luciferase assay. COS7 monkey kidney cells were cultured in a 24-well plate at $1.5 \times 10^5$ cells/well, and pGL3-PGC-1α-Luc plasmid (Addgene, Cambridge, Mass., USA) was transformed into cells using a Lipofector (Aptabio, Yongin, Republic of Korea). After transfection for 4 hours, the cells were allowed to stabilize for 24 hours.

And then, red bean ethanol extract manufactured from 100% ethanol in Example 1-2 was treated onto the cells at a concentration of 40 μg/mL for 24 hours. After the final 24 hours, the cells were lysed by dissolving in NP-40 buffer (ELPIS-Biotech), and the luciferase activity in the cell lysate was measured. The results are shown in FIG. 11.

Figure 11:
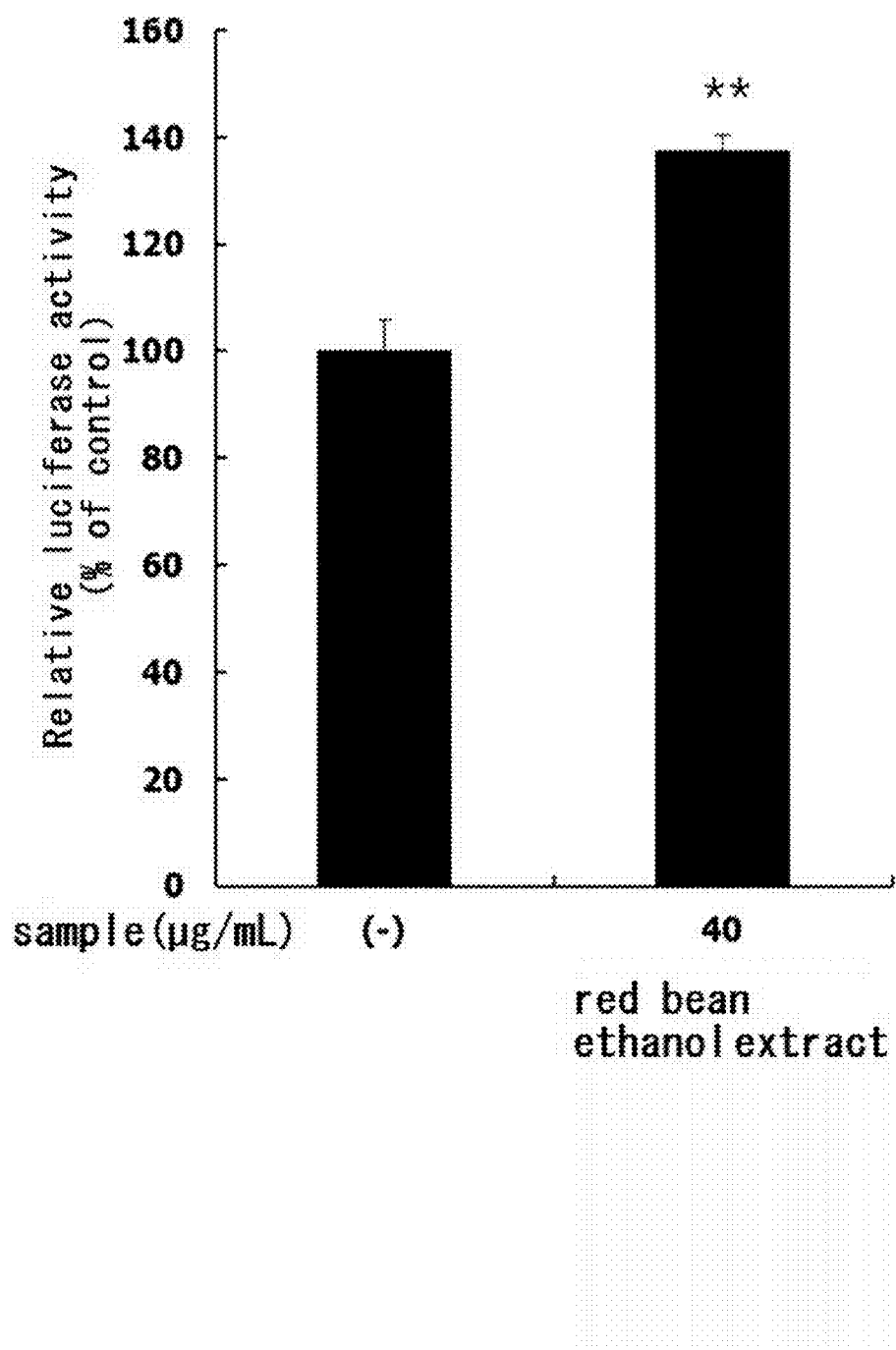
FIG. 11 shows the results of measuring an activity of PGC-1α after treatment with the ethanol extract red bean in COS-7 kidney cells.

As a result, as shown in FIG. 11, it was confirmed that the activity of PGC-1α, which is a major factor involved in exercise performance, is significantly increased (** $p<0.01$) by the red bean ethanol extract. Therefore, it was confirmed that red bean ethanol extract promotes exercise performance.

Figure 12:
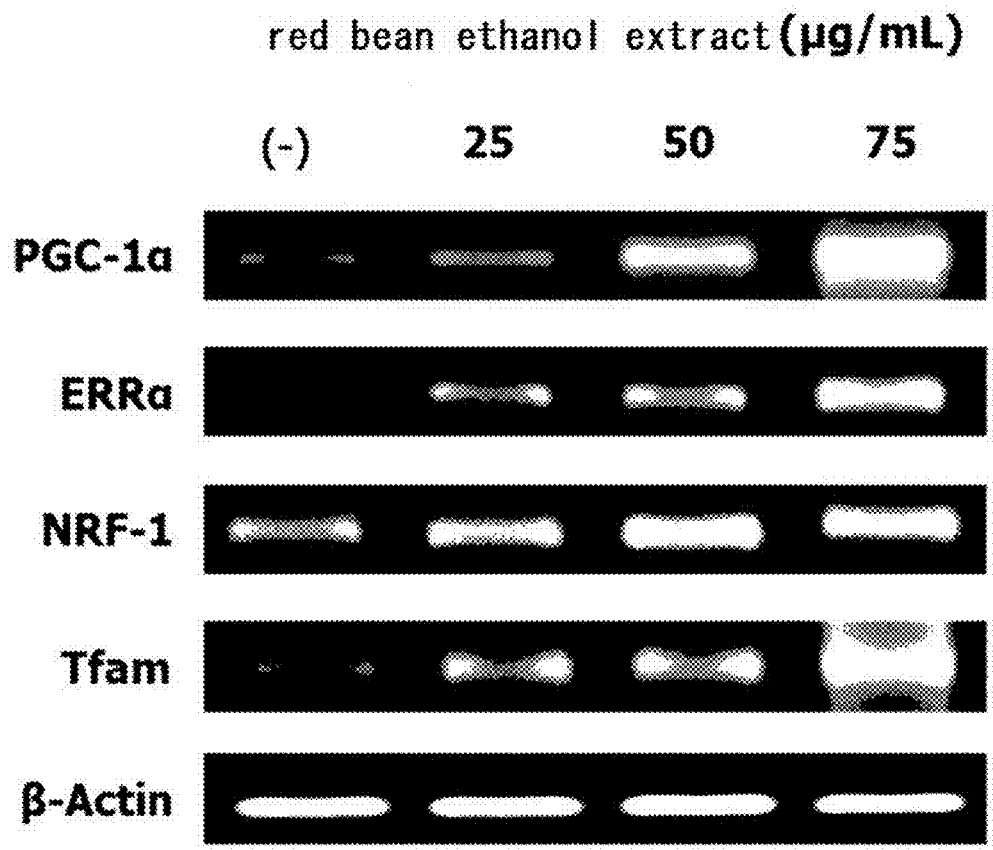
FIG. 12 shows the results of measuring mRNA expression levels of PGC-1α, ERRα, NRF-1 and Tfam, which are mitochondrial biosynthetic biomarkers, after treatment with the ethanol extract red bean in L6 muscle cells.

Experimental Example 12: Mitochondrial Biosynthesis Promotion Activity of Red Bean Ethanol Extract The experiment was carried out in the same manner as in Experimental Example 4. The red bean ethanol extract manufactured from 100% ethanol in Example 1-2 was dissolved at a concentration of 25, 50 or 40 μg/mL, and treated onto the cells to induce myotube differentiation. At this time, a group treated with 0.01% DMSO instead of the sample was used as a control group. Also in the RT-PCR, PCR was carried out using the following specific primers (Bioneer). The results are shown in FIG. 12.

TABLE 3

The primer sequences used for PCR in embodiments the present invention

| Amplified gene | Sequence name | SEQ ID NO: | Sequence | Direction |
|---|---|---|---|---|
| PGC-1α | PGC_F | SEQ ID NO: 11 | 5'-ATGTGTCGCCT TCTTGCTCT-3' | Forward |
|  | PGC_R | SEQ ID NO: 12 | 5'-ATCTACTGCCT GGGGACCTT-3' | Reverse |
| ERRα | ERR_F | SEQ ID NO: 13 | 5'-AAGGGGATGGA GACCACAGT-3' | Forward |
|  | ERR_R | SEQ ID NO: 14 | 5'-TGAGGTGGGAG CTGATAGGG-3' | Reverse |
| NRF-1 | NRF_F | SEQ ID NO: 15 | 5'-TGGACCCAAGC ATTACGGAC-3' | Forward |
|  | NRF_R | SEQ ID NO: 16 | 5'-GGTCATTTCAC CGCCCTGTA-3' | Reverse |

TABLE 3 -continued

The primer sequences used for PCR in embodiments the present invention

| Amplified gene | Sequence name | SEQ ID NO: | Sequence | Direction |
|---|---|---|---|---|
| Tfam | Tfam_F | SEQ ID NO: 17 | 5'-GCTTCCAGGAG GCTAAGGAT-3' | Forward |
|  | Tfam_R | SEQ ID NO: 18 | 5'-CCCAATCCCAA TGACAACTC-3' | Reverse |
| β-Actin | Actin_F | SEQ ID NO: 5 | 5'-CTGTGTGGATT GGTGGCTCTAT-3' | Forward |
|  | Actin_R | SEQ ID NO: 6 | 5'-GTGTAAAACGC AGCTCAGTAACA3' | Reverse |

As a result, as shown in FIG. 12, it was confirmed that mRNA expression of PGC-1α, ERRα, NRF-1 and Tfam was increased by treatment with red bean ethanol extract. This means that the red bean ethanol extract of the present invention has an excellent ability to increase the expression of mitochondrial biosynthesis-related genes, which are closely related to exercise performance.

Experimental Example 13: Enhancement of Exercise Performance of Red Bean Protein and Peptide In the same manner as in Experimental Example 11, the PGC-1α activity was evaluated by treating 40 μg/mL of the red bean protein and red bean peptide manufactured in Example 2-1, 2-4, 2-5, and 2-6, respectively. The results are shown in FIG. 13.

Figure 13:
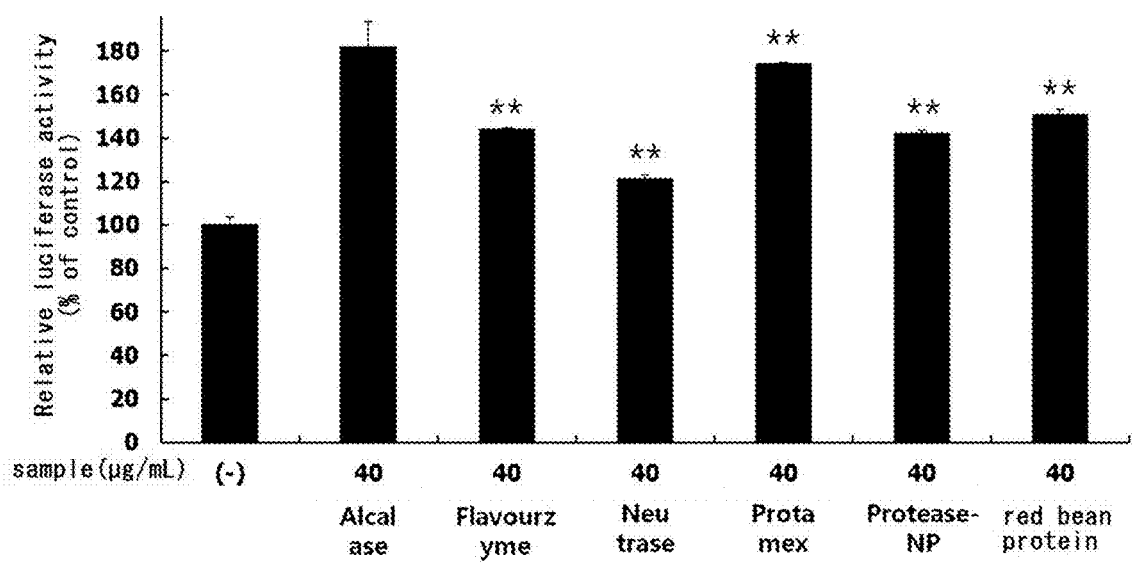
FIG. 13 shows the results of measuring an expression level of PGC-1α, after treatment with red bean protein and red bean peptide by enzymatic reaction in L6 muscle cells, respectively.

As a result, as shown in FIG. 13, it was confirmed that the activity of PGC-1α, which is a major factor involved in exercise performance, is significantly increased (** p<0.01) by the red bean protein and the red bean peptide. Therefore, it was confirmed that the red bean protein and the red bean peptide promotes exercise performance.

Experimental Example 14: Mitochondrial Biosynthesis Promotion Activity of Red Bean Peptide In the same manner as in Experimental Example 4, the red bean peptide manufactured in Example 2-5 was treated with 50 or 100 μg/mL to evaluate mitochondrial biosynthesis activity of red bean peptide. The results are shown in FIG. 14.

Figure 14:
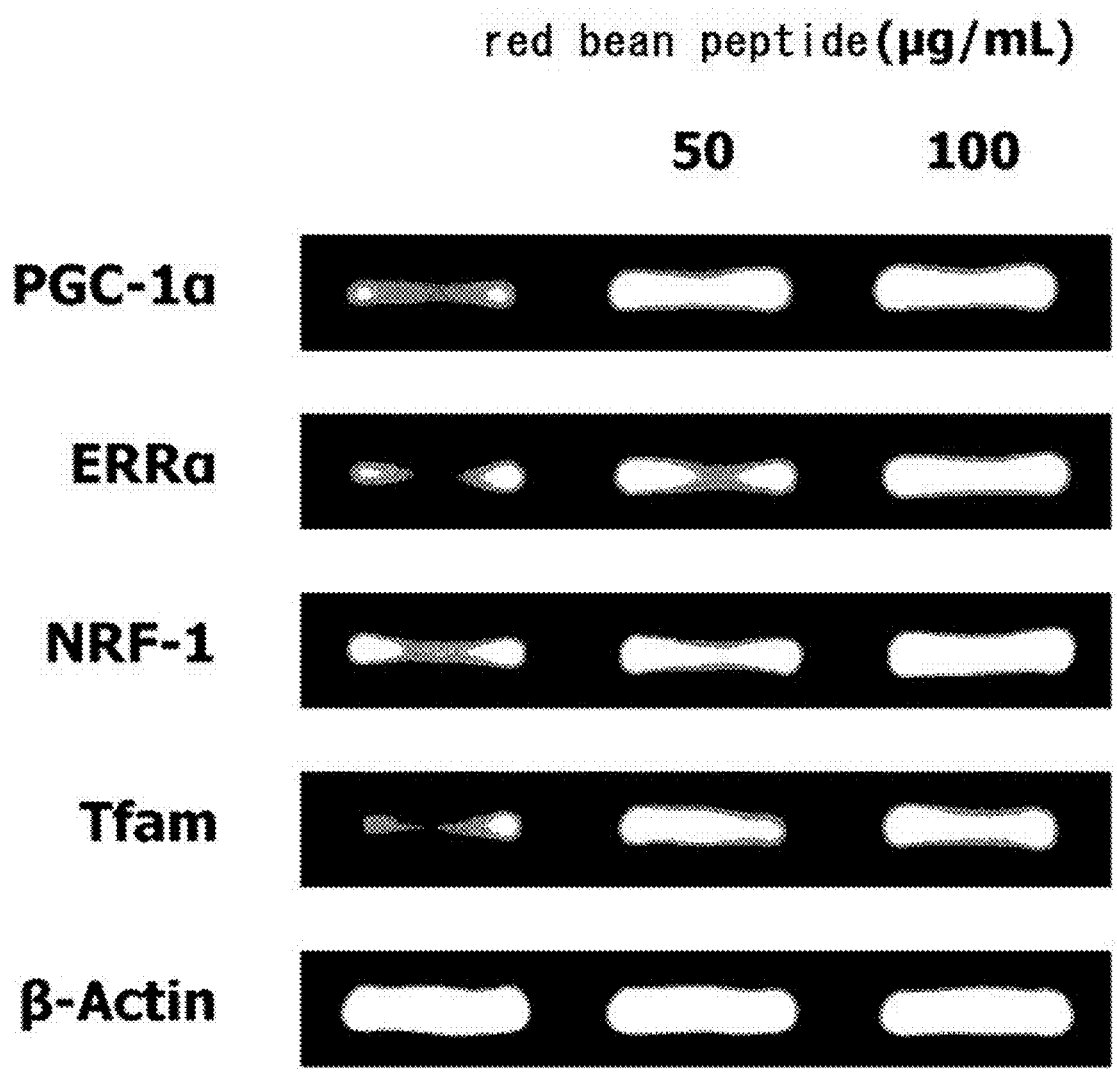
FIG. 14 shows the results of measuring mRNA expression levels of PGC-1α, ERRα, NRF-1 and Tfam, which are mitochondrial biosynthetic biomarkers, after treatment with red bean peptide in L6 muscle cells.

As a result, as shown in FIG. 14, it was confirmed that mRNA expression of PGC-1α, ERRα, NRF-1 and Tfam was increased by treatment with red bean peptide. This means that the red bean peptide of the present invention has an excellent ability to increase the expression of mitochondrial biosynthesis-related genes, which are closely related to exercise performance.

Experimental Example 15: Enhancement of Exercise Performance of Black Bean Ethanol Extract In the same manner as in Experimental Example 11, the PGC-1α activity was evaluated by treating 40 μg/mL of the black bean ethanol extract manufactured in Example 3-2. The results are shown in FIG. 15.

Figure 15:
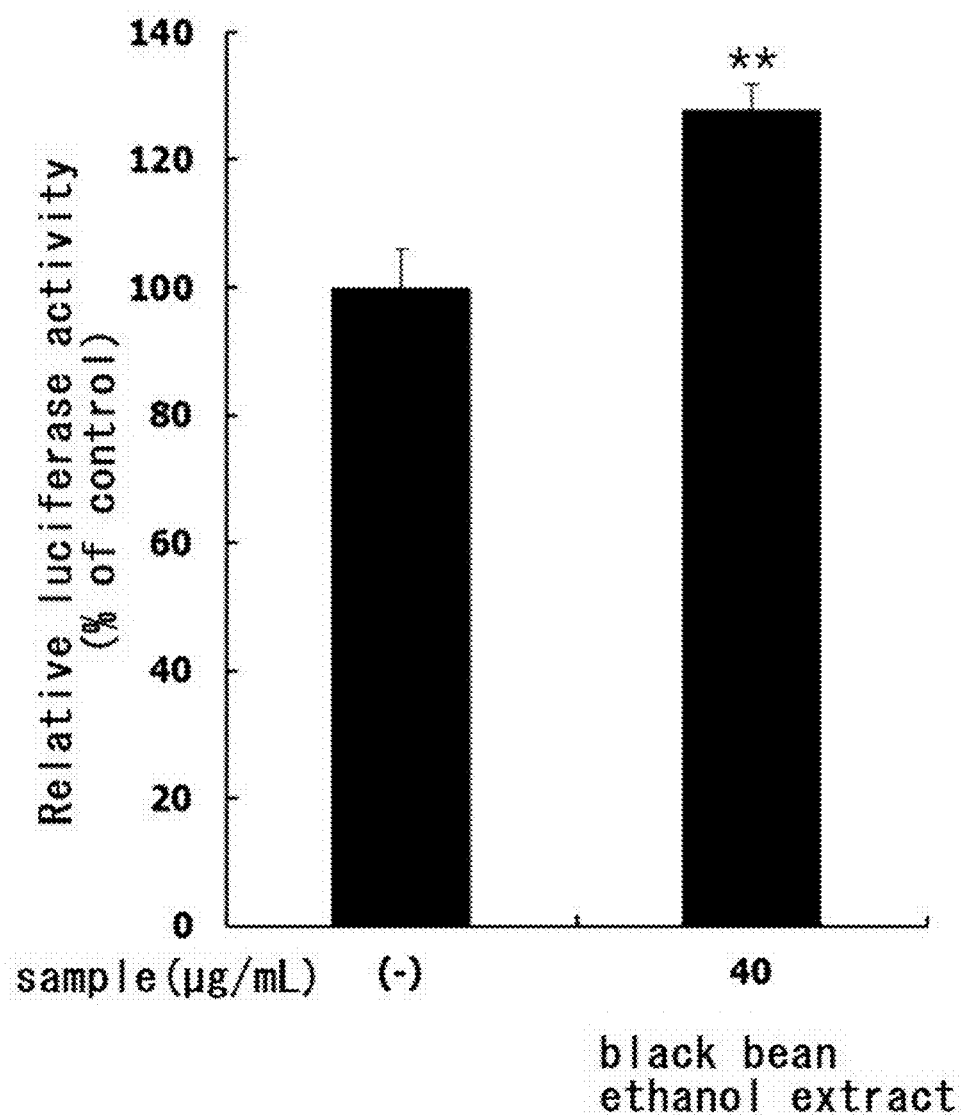
FIG. 15 shows the results of measuring an activity of PGC-1α after treatment with the ethanol extract black bean in COS-7 kidney cells.

As a result, as shown in FIG. 15, it was confirmed that the activity of PGC-1α, which is a major factor involved in exercise performance, is significantly increased (** p<0.01) by the black bean ethanol extract. Therefore, it was confirmed that the black bean ethanol extract promotes exercise performance.

Experimental Example 16: Anti-Atrophy Activity of Red Bean Peptide 16-1. Animal Breeding and Induction of Muscle Atrophy Seven weeks old male mice (C57BL/6N; Young Bio) were purchased for experiment was carried out. Breeding of all animals was carried out at the Yonsei Laboratory Animal Reaserch Center (YLARC, Seoul, Republic of Korea), the breeding environment was maintained at a temperature of 23±2° C. and a relative humidity of 55±10%. Before the start of the experiment, a total of 20 mice were randomly divided into groups of 5 mice each group, i, e., normal group, atrophy group, red bean 300 group, and red bean 600 group, respectively. After one week of adaptation, anesthesia was induced by intraperitoneal injection of 325 mg/kg of tribromoethanol (Sigma-aldrich). After anesthesia, the right hind limb gastrocnemius muscle and the right footpad of mice in the atrophy group and red bean groups were stapled using a skin stapler (Unidus, Chungcheongbuk-do, Republic of Korea) to damage the muscles and the right hind limb was prevented from moving, and this state was maintained for a week. After one week, the staples fixed to the gastrocnemius muscle and the footpad of mice were removed, and the recovery was induced by daily oral administration of the red bean ethanol extract manufactured with 50% ethanol in Example 1-2 at a concentration of 300 mg/kg or 600 mg/kg for a week. At this time, the normal group and the atrophy group were orally administered with saline instead of the test sample.

16-2 Muscle Strength Measurement

At the end of the oral administration period, the muscle strength of the mice was measured using a muscle strength meter (Chatillon force measurement system; Columbus Instrument, Columbus, Ohio, USA). Until the mouse released the bar of the strength meter, the tail of the mouse was pulled with constant force, and a total of 5 consecutive tests were carried out per mouse.

Figure 16:
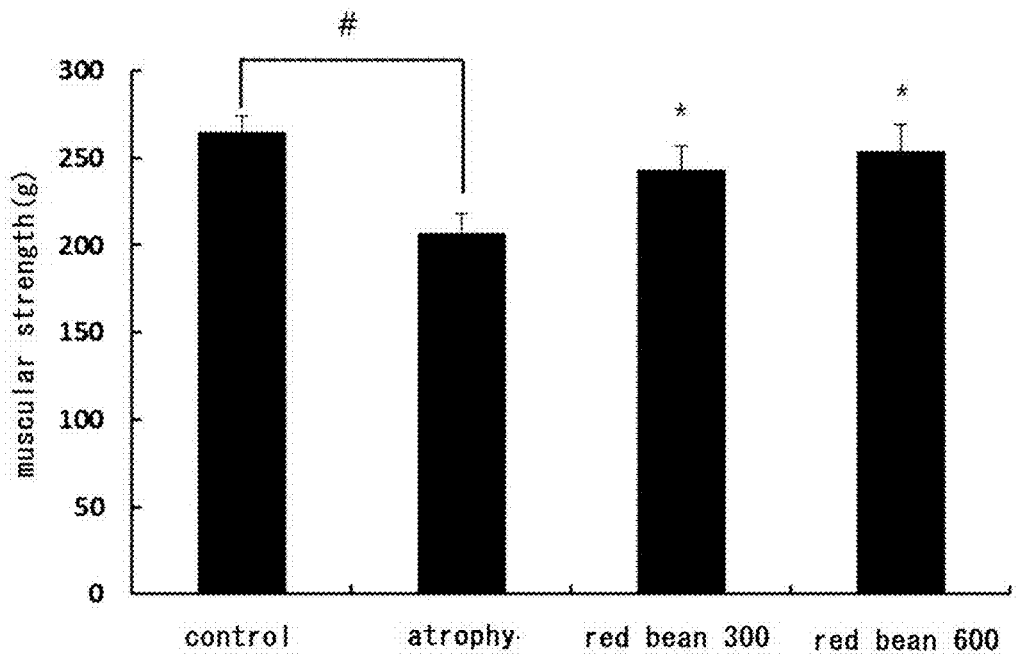
FIG. 16 shows the result of measuring a muscle strength after treatment with the ethanol extract red bean in muscle atrophy-induced mice.

As a result, as shown in FIG. 16, muscle strength was significantly decreased (# p<0.05) in atrophy group compared to normal group, whereas muscle strength was significantly increased (* p<0.05) by treatment with red bean ethanol extract. This means that the red bean ethanol extract of the present invention has an excellent effect of increasing muscle strength which is reduced due to the atrophy.

16-3. Endurance Measurement

The exercise performance of the experimental animals was evaluated using a treadmill (LE8710MTS; Panlab, Barcelona, Spain). Starting at a speed of 8 m/min initially, the speed was increased by 1 m/min every minute. When the mice reached the shock grid, it was set to emit 0.2 mA of electricity to the mice, and the experiment was stopped at the point when the mice did not run any longer after receiving the electric shock for 10 seconds, followed by measuring the time and distance.

Figure 17A:
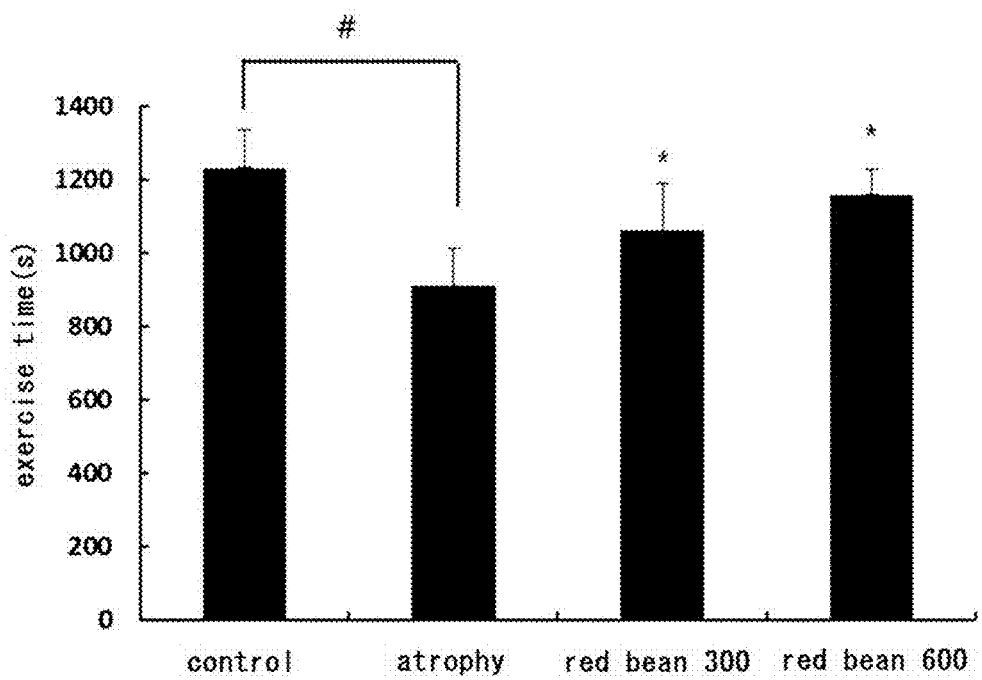
FIGS. 17A and 17B shows the result of measuring the endurance after treatment with the ethanol extract red bean in muscle atrophy-induced mice (a: exercise time, b: exercise distance).
Figure 17B:
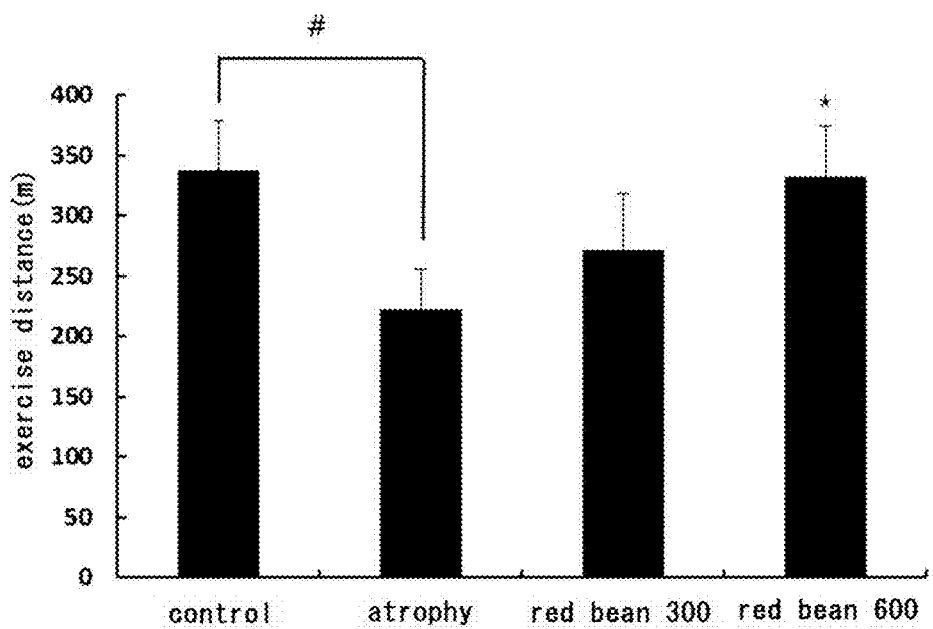

As a result, as shown in FIGS. 17A and 17B, the exercise distance and time were significantly decreased (# p<0.05) in atrophy group compared to normal group, where are the exercise distance and the exercise time were significantly increased (* p<0.05) by treatment with red bean ethanol extract. This means that the red bean ethanol extract of the present invention has an excellent effect of improving the exercise performance which is decreased due to the atrophy.

16-4. Muscle Weight Measurement

After measuring muscle strength and exercise performance, the experimental animals were anesthetized with intraperitoneal injection of 325 mg/kg of tribromomethanol (Sigma-aldrich) and sacrificed via heart blood collection. After confirming that the heart was stopped, the tibialis anterior muscle, which was not injured in the right hind limb, was removed and measured the weight.

Figure 18:
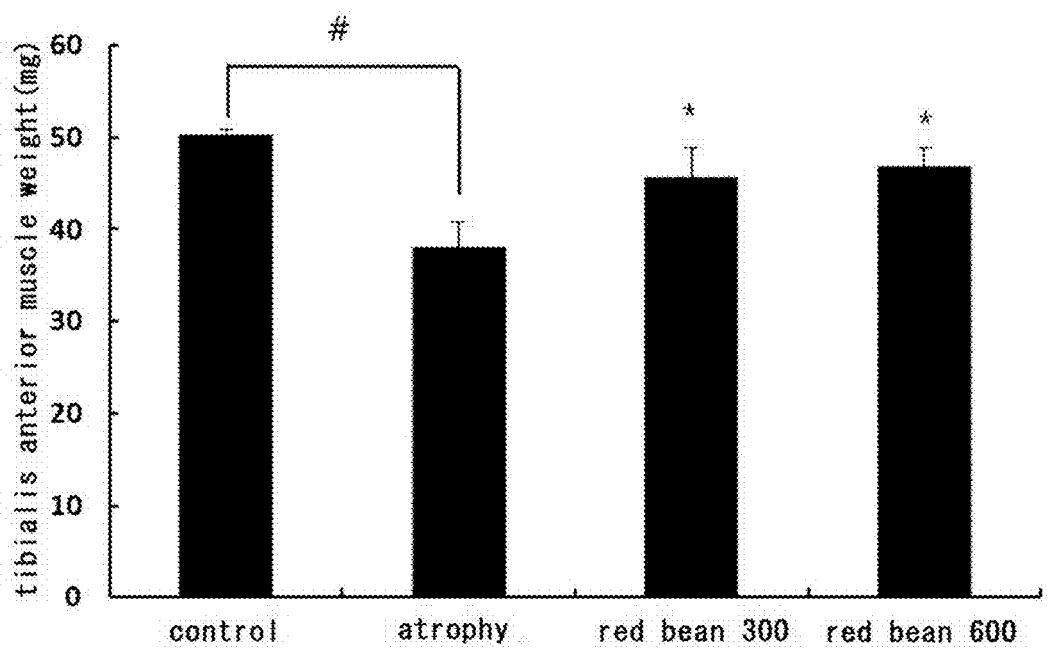
FIG. 18 shows the result of measuring the weight of the tibialis anterior muscle after treatment with the ethanol extract red bean in muscle atrophy-induced mice.

As a result, as shown in FIG. 18, the weight of the tibialis anterior muscle of the atrophy group, which was not injured, was significantly decreased (# $p<0.05$) compared with the normal group, but the weight was significantly increased (* $p<0.05$) by treating the bean ethanol extract. This means that the red bean ethanol extract of the present invention has an excellent effect of increasing the weight of muscles which is reduced due to the atrophy.

Hereinafter, preparation examples of foods and pharmaceuticals for improving muscular function or for enhancing exercise performance comprising the red bean as an active ingredient according to the present invention will be described, but the present invention is not intended to be limited thereto but is only specifically described. Using the red bean ethanol extract having excellent effect of improving muscular function or enhancing exercise performance, the pharmaceuticals and food compositions of Preparation Examples 1 and 2 were manufactured according to the conventional methods, according to the following composition components and ratios.

Preparation Example: Pharmaceuticals

Preparation Example 1-1 Powder

After mixing 50 mg of red bean extract, red bean peptide, black bean extract or black bean peptide of Examples 1 to 4, 2 g of crystalline cellulose, the powder was filled in an airtight container according to a conventional powder preparation method to prepare a powder.

Preparation Example 1-2. Tablet

After mixing 50 mg of red bean extract, red bean peptide, black bean extract or black bean peptide of Examples 1 to 4, 400 mg of crystalline cellulose, and 5 mg of magnesium stearate, the tablets were manufactured by tableting according to a conventional tablet preparation method.

Preparation Example 1-3. Capsule

After mixing 30 mg of red bean extract, red bean peptide, black bean extract or black bean peptide of Examples 1 to 4, 100 mg of whey protein, 400 mg of crystalline cellulose, and 6 mg of magnesium stearate, the capsules were filled in gelatin capsules according to a conventional capsule preparation method.

Preparation Example 2: Foods

Preparation Example 2-1. Manufacture of Health Food

The health food composition of the present invention may be preparation by mixing 1000 mg of red bean extract, red bean peptide, black bean extract or black bean peptide of Examples 1 to 4, respectively, 70 ug of vitamin A acetate, 1.0 mg of vitamin E, 0.13 mg of vitamin B1, 0.15 mg of vitamin B2, 0.5 mg vitamin B6, 0.2 ug of vitamin B12, 10 mg of vitamin C, 10 ug of biotin, 1.7 mg of nicotinic acid amide, 50 ug of folate, 0.5 mg of calcium pantothenate, 1.75 mg of ferrous sulfate, 0.82 mg of zinc oxide, 25.3 mg of magnesium carbonate, 15 mg of monobasic potassium phosphate, 55 mg of dibasic potassium phosphate, 90 mg of potassium citrate, 100 mg of calcium carbonate, 24.8 mg of magnesium chloride may be mixed, while the compounding ratio thereof may be arbitrarily modified. The above components may be mixed according to a conventional method to produce granules for preparing a health food composition according to a conventional method.

Preparation Example 2-2. Manufacture of Health Beverages 1000 mg of red bean extract, red bean peptide, black bean extract or black bean peptide of Examples 1 to 4, respectively, 1000 mg of citric acid, 100 g of oligosaccharides, 2 g of plum concentrate, 1 g of taurine were added to purified water, and the above components were mixed in a total of 900 mL according to a conventional health drink manufacturing method, after stirring and heating at 85° C. for about 1 hour, the resulting solution is filtered, taken in a sterilized 2 L vessel, sealed sterilized, refrigerated and then used in the preparation of a health beverage composition.

Preparation Example 2-3. Chewing Gum

Chewing gum was prepared in a conventional manner by mixing 20 wt % of a gum base, 76.9 wt % of sugar, 1 wt % of a flavor and 2 wt % of water, and 0.1 wt % of a red bean extract, red bean peptide, black bean extract or black bean peptide of Examples 1 to 4, respectively.

Preparation Example 2-4. Candy

Candy was prepared in a conventional manner by mixing 60 wt % of sugar, 39.8 wt % of starch syrup, 0.1 wt % of flavor and 0.1 wt % of the red bean extract, red bean peptide, black bean extract or black bean peptide of Examples 1 to 4, respectively.

Preparation Example 2-5. Biscuit

Biscuit was prepared in a conventional manner by mixing 25.59 wt % of soft flour, 22.22 wt % of plain flour, 4.80 wt % of refined sugar, 0.73 wt % of salt, 0.78 wt % of glucose, 11.78 wt % of palm shortening, 1.54 wt % of ammonium, 0.17 wt % of sodium bicarbonate, 0.16 wt % of sodium bisulfite, 1.45 wt % of rice flour, 0.0001 wt % of vitamin B, 0.04 wt % of milk flavor, 20.6999 wt % of water. 1.16 wt % of milk powder, 0.29 wt % of substitute powder milk, 0.03 wt % of Monobasic Calcium phosphate, 0.29 wt % of spray salt and 7.27 wt % of oil mist, and 1.00 wt % of the red bean extract, red bean peptide, black bean extract or black bean peptide of Examples 1 to 4, respectively.

What is claimed is:

1. A method for treating a muscle disorder, enhancing exercise performance or improving muscular function in a subject in need thereof, the method comprising administering a composition comprising a therapeutically effective amount of a hexane extract of a red bean (*Vigna angularis*), a red bean-derived protein or a red bean-derived peptide as an active ingredient to the subject to treat the muscle disorder or enhance the enhancing exercise performance.

2. The method of claim 1, wherein the red bean-derived protein is obtained by a process comprising the following steps i) to v), and wherein the red bean-derived peptide is obtained by a process comprising the following steps i) to vii):

i) crushing a dried red bean, followed by extraction with hexane as a solvent;

ii) removing the hexane extract obtained in step i), and adding water to the residue, wherein the DH of the aqueous mixture is pH of 7.0 to 10.0;

iii) obtaining a supernatant by centrifuging the solution made in step ii);

iv) adjusting the pH of the supernatant obtained in step iii) to pH 2.0 to 6.0;

v) centrifuging the supernatant obtained in step iv) to obtain a precipitate as a red bean-derived protein;

vi) adding a hydrolase to the red bean-derived protein obtained in step v) to cause an enzymatic reaction, followed by filtering the reaction mixture to remove the precipitate made in the reaction; and vii) lyophilizing the filtrate made in step (vi), so as to obtain the peptide.

3. The method of claim 2, wherein the hydrolase of step vi) is at least one protein hydrolase selected from the group consisting of Alcalase, Flavourzyme, Neutrase, Protamex and Protease-NP.

4. The method of claim 1, wherein the red bean is one or both selected from the group consisting of red bean (*V. angularis* W.F.Wight) and black bean (*V. angularis* var. *angularis*).

5. The method of claim 1, wherein the muscle disorder is a muscle disorder caused by a decrease in muscle function, muscle wasting or muscle degeneration.

6. The method of claim 5, wherein the muscle disorder is selected from the group consisting of atony, muscular atrophy, muscular dystrophy, myasthenia gravis, cachexia, and sarcopenia.

7. The method of claim 1, wherein the improvement in exercise performance includes the treatment of at least one disease selected from the group consisting of degenerative disease, mitochondrial disorder, endurance dysfunction, agility dysfunction, lethargy, muscle loss and depression.

8. The method of claim 1, wherein the composition is a pharmaceutical composition or a food composition.

* * * * *